(12) United States Patent
Moon

(10) Patent No.: US 11,642,498 B2
(45) Date of Patent: May 9, 2023

(54) ISOLATING DRAINAGE CATHETER

(71) Applicant: Bioflow Inc, Atlanta, GA (US)

(72) Inventor: John T. Moon, Atlanta, GA (US)

(73) Assignee: Bioflow Inc, Atlanta, GA (US)

( * ) Notice: Subject to any disclaimer, the term of this patent is extended or adjusted under 35 U.S.C. 154(b) by 99 days.

(21) Appl. No.: 17/185,631

(22) Filed: Feb. 25, 2021

(65) Prior Publication Data

US 2021/0260346 A1 Aug. 26, 2021

Related U.S. Application Data

(60) Provisional application No. 62/981,038, filed on Feb. 25, 2020.

(51) Int. Cl.
*A61M 25/10* (2013.01)
*A61M 39/10* (2006.01)
*A61M 1/00* (2006.01)

(52) U.S. Cl.
CPC .............. *A61M 25/10* (2013.01); *A61M 1/84* (2021.05); *A61M 39/10* (2013.01); *A61M 2039/1038* (2013.01); *A61M 2205/02* (2013.01); *A61M 2210/1082* (2013.01)

(58) Field of Classification Search
CPC .......... A61M 25/10; A61M 39/10; A61M 2039/1038; A61M 2205/02; A61M 2210/1082; A61M 25/0111; A61M 25/0119; A61M 25/0017; A61M 27/00
See application file for complete search history.

(56) References Cited

U.S. PATENT DOCUMENTS

| | | | |
|---|---|---|---|
| 4,324,262 A | 4/1982 | Hall | |
| 5,171,305 A | 12/1992 | Schickling et al. | |
| 6,749,584 B2 | 6/2004 | Briggs et al. | |
| 7,615,034 B2 | 11/2009 | DiFiore | |
| 7,789,893 B2* | 9/2010 | Drasler | A61B 17/0057 606/213 |
| 8,617,104 B2* | 12/2013 | Yribarren | A61M 25/1006 604/103.05 |
| 9,427,244 B2* | 8/2016 | Lund-Clausen | A61B 17/221 |
| 9,987,449 B2* | 6/2018 | Vitullo | A61M 16/0463 |

(Continued)

FOREIGN PATENT DOCUMENTS

| | | | |
|---|---|---|---|
| EP | 0792656 B1 | 7/2003 | |
| GB | 2484598 A * | 4/2012 | A61M 25/00 |

(Continued)

OTHER PUBLICATIONS

Jul. 2, 20210—(WO) ISR & WO—App. No. PCT/US21/19682.

*Primary Examiner* — Susan S Su
*Assistant Examiner* — Eric Rassavong
(74) *Attorney, Agent, or Firm* — Banner & Witcoff, Ltd.

(57) ABSTRACT

Aspects of this disclosure relate to catheter assemblies, that include an inner tube component, an outer tube component that fits over the inner tube component, and a disposable layer of film that isolates the otherwise fluid-exposed portions of the catheter from the fluid it drains. This disposable film can be removed at regular intervals and obviates the need for catheter exchanges as the isolating disposable film, rather than the catheter itself, is removed. The principal characteristic of the disposable film is that it is relatively impermeable to fluid, for example, bodily fluids.

15 Claims, 20 Drawing Sheets

(56) References Cited

U.S. PATENT DOCUMENTS

| | | | |
|---|---|---|---|
| 10,010,335 B2* | 7/2018 | Greenhalgh | A61B 17/22 |
| 10,028,759 B2* | 7/2018 | Wallace | A61B 17/221 |
| 10,905,860 B2* | 2/2021 | Goto | A61B 17/12109 |
| 11,291,434 B2* | 4/2022 | Magana | A61B 90/39 |
| 2017/0136209 A1* | 5/2017 | Burnett | A61M 1/0001 |
| 2019/0105465 A1* | 4/2019 | Erbey, II | A61M 1/74 |
| 2019/0358432 A1* | 11/2019 | Johnson | A61M 25/0082 |

FOREIGN PATENT DOCUMENTS

| | | | |
|---|---|---|---|
| WO | WO-2018212126 A1 * | 11/2018 | A61M 25/0045 |
| WO | 2019/046800 A1 | 3/2019 | |

* cited by examiner

Detail A

Detail B

Section A-A

Section B-B

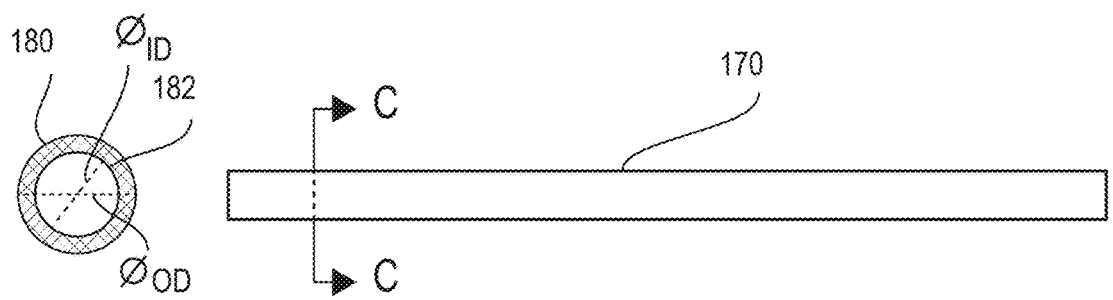
FIG. 23
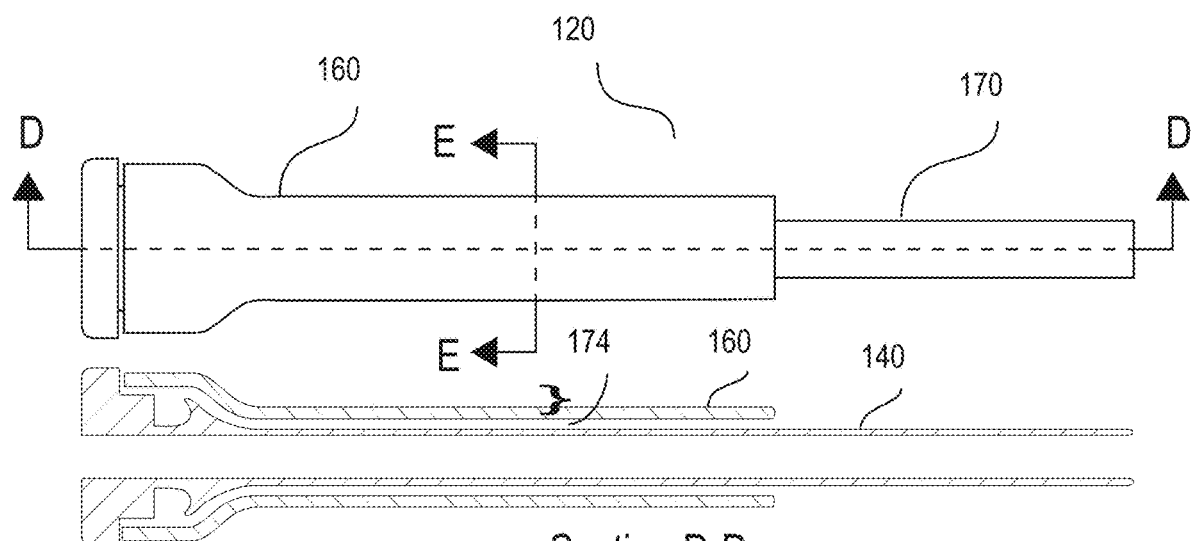
FIG. 24
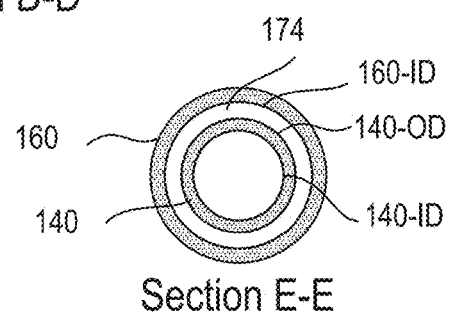

ISOLATING DRAINAGE CATHETER

CROSS-REFERENCE TO RELATED APPLICATIONS

This application claims priority to U.S. Provisional Patent Application No. 62/981,038, filed Feb. 25, 2020, which is incorporated herein by reference in its entirety and made a part hereof.

FIELD OF THE INVENTION

The present invention relates to drainage catheter assemblies.

BACKGROUND

Drainage catheters are one of the most commonly utilized medical devices, yet face significant complications resulting from catheter occlusion. Drainage catheter assemblies are useful in providing flow diversion when natural body conduits are obstructed and lead to pathologic build-up of fluid and pressure. Drainage catheter assemblies provide an outlet when the natural outlet lumen is compromised due to pathology, obstructed, or otherwise unable to be regulated. For example, drainage catheters assemblies can be used to provide a percutaneous outlet for urine collected in a hydronephrotic kidney, resulting from a distal ureteral obstruction by a kidney stone.

Percutaneous nephrostomy (PCN) catheter placement is a common, minimally invasive surgical procedure whereby a tube is placed through the skin and into the kidney to decompress the kidney from irreversible distending injury (from urine back-pressure) due to urinary obstructions by allowing for urinary diversion to an external urine bag. However, these catheters are prone to bacterial invasion and encrustation (from urine mineral deposits). A build-up of bacteria and mineral deposits within the catheter can lead to blockage of draining and subsequent clinical infection in as much as 20% of patients.

For the patient, this may mean an infection requiring emergent hospital admission and a repeat surgery with all the associated risks of re-operation. For healthcare systems, this means poorer healthcare outcomes and additional healthcare expenditures related to (1) an infectious complication and (2) re-operation.

Existing catheter assemblies used for drainage are single tube and single lumen with a distal end lumen with a limited number of discrete side-holes extending through the tubular shaft wall. These catheter assemblies are retained within the specified space via Cope loop assembly, Malecot tip assembly, or other similar anti-dislodgement catheter tip assemblies.

As with any catheter assembly, the need to maintain the structural integrity, sterility, and patency are critically important to the catheter assembly's functional application. The present inventor recognizes, among other things, that current standard-of-care drainage catheter assemblies may be prone to blockage at, for example, and around the distal portions of the catheter exposed to the body environment as well as along any point the drained material courses from the draining lumen(s) throughout the catheter assembly. Blockage complications may be a result of biofilm accumulation, mineral encrustation, biological stones, and accumulation of other debris, among other things. Prolonged blockage without resolution may lead to infection, organ damage, sepsis, and other associated complications.

To resolve complications related to blockage, existing catheter assemblies might be manipulated, repositioned, or exchanged and replaced. They may also be de-clogged mechanically, or by use of chemicals. Repeat procedures require patients to undergo anesthesia, which subjects them to associated risks.

Though existing drainage catheter assemblies can provide effective means to, for example, drain internal cavities or organs, there exists a need in the art to improve drainage catheters and the techniques used to provide the desired drainage. Aspects of the present invention provide improvements to the existing art of drainage catheters and their methods of use.

These features, along with many others, are discussed in greater detail below.

SUMMARY

In light of the foregoing background, the following presents a simplified summary of the present disclosure in order to provide a basic understanding of some aspects of the invention. This summary is not an extensive overview of the invention. It is not intended to identify key or critical elements of the invention or to delineate the scope of the invention. The follow summary merely presents some concepts of the invention in a simplified form as a prelude to the more detailed description provided below.

Aspects of this disclosure relate to a catheter assembly comprising: an elongated outer tube component having a proximal end and a distal end; an elongated inner tube component having a proximal end and a distal end, and positioned within the elongated outer tube component; and an isolating medium positioned over the elongated inner tube component isolating at least the distal end of the elongated inner tube component from bodily fluids.

In other aspects of the invention, the isolating medium may comprise a removable isolating medium. Additionally, the catheter assembly may further comprise a locking mechanism located between the inner tube component and the outer tube component. The locking mechanism may be a lock and key mechanism between the inner tube component and the outer tube component. Further, the locking mechanism may be a screw connector between the inner tube component and the outer tube component. Additionally, at least one of the elongated outer tube component and the elongated inner tube component may comprise a cavity for the isolating medium. The catheter assembly may further comprise a drainage catheter assembly that may be utilized for a kidney. The catheter assembly may further comprise a treatment catheter assembly with a fluid treatment. The fluid treatment comprises one of a liquid treatment and a gas treatment. The isolating medium may comprise a plastic material. Additionally, the catheter assembly may comprise an anti-dislodgement mechanism that includes at least two arms located in one of the inner tube component or the outer tube component. The catheter assembly may further comprise an anti-dislodgement mechanism that includes an inflatable balloon located in one of the inner tube component or the outer tube component.

Additional aspects of this disclosure may relate to a method of introducing or removing a fluid from a body cavity, the method comprising: inserting a catheter assembly into a body cavity; withdrawing a bodily fluid from the body cavity; and removing the isolating medium from at least the distal end of the inner tube component. The isolating medium is pulled from the proximal end of the inner tube, and removes the isolating medium at least from the material reservoir to the distal end of the inner tube, and the isolating medium at least from the distal end of the inner tube to the proximal end or hub of the inner tube. The catheter assembly may comprise: an outer tube component having a proximal end and a distal end; an inner tube component having a proximal end and a distal end, and positioned within the outer tube component; and an isolating medium positioned over the inner tube component isolating at least the distal end of the inner tube component from bodily fluids. The isolating medium may comprise a first isolating medium, and wherein the method further comprises replacing the first isolating medium with a second isolating medium, different from the first isolating medium. The first isolating medium may be connected to the second isolating medium, wherein replacing the first isolating medium with the second isolating medium comprises extracting the first isolating medium from the catheter assembly and therein drawing the second isolating medium over at least the distal end of the elongated inner tube component.

Still other aspects of this disclosure may relate to an isolating medium for a catheter comprising an elongated, flexible, tubular structure having an open first end and an open second end, opposing the first end, wherein the open first end is attachable to a catheter. The isolating medium may comprise a separable medium that is separable when exposed to a predetermined axial tension.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

FIG. 23 illustrates the geometry and relative size of the isolating material medium as they relate to catheter assembly according to at least one embodiment of the invention. Section C-C of FIG. 23 illustrates a cross sectional view of one possible embodiment of tubular isolating medium.

FIG. 24 illustrates the geometry and relative size of the isolating material medium as they relate to catheter assembly according to at least one embodiment of the invention. Section D-D of FIG. 24 illustrates a cross section view catheter assembly. Section E-E of FIG. 24 illustrates a cross sectional view of the catheter assembly as one example of geometric constraints that may influence the geometry for tubular isolating material.

Figure 1:
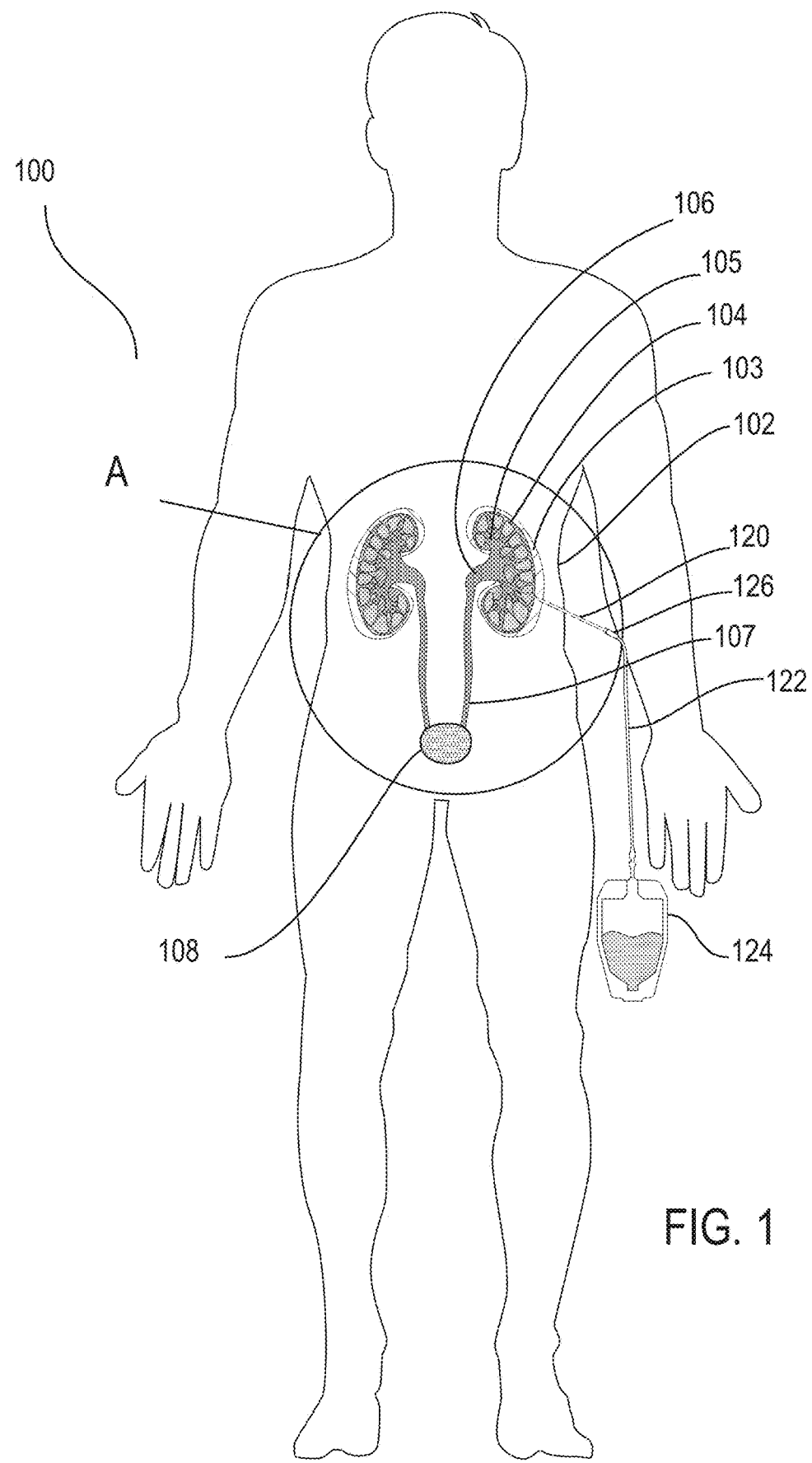
FIG. 1 is a schematic illustration of a drainage catheter assembly according to one embodiment of the invention.

The drawing figures are not necessarily to scale. Certain features and components may be shown exaggerated in scale or in schematic form and some details may not be shown in the interest of clarity and conciseness.

DETAILED DESCRIPTION OF EMBODIMENTS

In the following description of various examples of the invention, reference is made to the accompanying drawings, which form a part hereof, and in which are shown by way of illustration various example structures, systems, and steps in which aspects of the invention may be practiced. It is to be understood that other specific arrangements of parts, structures, example devices, systems, and steps may be utilized and structural and functional modifications may be made without departing from the scope of the present invention.

The current paradigm for drainage catheters involve (1) initial placement followed by (2) replacement or exchanges. Replacements or exchanges occur at regular 3-month intervals or may be required emergently when catheter occlusion leads to infectious complications. Given the challenge biofilm formation and encrustation currently pose in the catheter landscape, the catheter assembly as described herein offers a radically novel mechanism to prophylactically remove accumulating debris at regular intervals, preventing catheter obstruction, and ultimately preventing downstream infection. Where current catheters require placement and regular or emergent replacement, the catheter assembly as described herein can be placed once and its anti-occlusion mechanism can allow for an extended catheter life of at least 1 or more equivalent catheter replacements.

Broadly speaking, the catheter assembly as described herein provides a barrier between the fluid it drains and the catheter itself. This barrier is composed of a disposable polyurethane film that extends from a reservoir within the catheter to cover and isolate the inner tube of the drainage catheter. The catheter assembly as described herein allows for this film to be simultaneously removed and replaced while keeping the catheter within the target organ. This disposable film can be removed at regular intervals to prevent the accumulation of debris. The film, rather than the catheter itself, is removed through a mechanical replacement mechanism built into the device. The catheter assembly as described herein includes an anti-occlusion mechanism obviates the need for catheter exchanges in the operating room. The catheter material reservoir may contain enough disposable film that would be equivalent to at least 1 or more catheter exchanges.

In order to minimize complications related to catheter assembly blockage from occurring, the present invention comprises catheter assemblies, that include an inner tube component, an outer tube component that fits over the inner tube component, and a disposable layer of film that isolates the otherwise fluid-exposed portions of the catheter from the fluid it drains. This disposable film can be removed at regular intervals and obviates the need for catheter exchanges as the isolating disposable film, rather than the catheter itself, is removed. The principal characteristic of the disposable film is that it is relatively impermeable to fluid, for example, bodily fluids, as well as relatively impermeable to gases.

The following catheter assembly can be inserted into body conduits, body cavities, or other target organs (such as the kidney, bladder, chest cavity, or lung/airways), to relieve obstruction, allow for fluid or gas diversion, provide access for other procedures, or administer fluids or gases for therapeutic or diagnostic purposes, among other potential uses. This minimally invasive catheter assembly obviates the need for open and invasive surgical procedures.

One embodiment of the invention is a drainage catheter assembly comprising: an inner tube; an outer tube; an interspace between the inner and outer tube; a hub at the proximal end of the drainage catheter that can connect the inner and outer tube; and, a hub that can contain a film contained within a geometrically accommodating reservoir. For example, a finger-cot organized film as shown by material reservoir. The material within the material reservoir feeds material over the proximal portions of the catheter shaft. It then extends to the distal portion of the catheter shaft. Because the outer tube is shorter in length than the inner tube, the tubular material is visualized as it travels to the distal portion of the catheter. As the tubular material travels to the distal tip, it then inverts its direction of travel into the draining lumen of the catheter. There, it covers the distal to proximal portions of the draining lumen, and becomes visible as it exits the proximal hub into a connecting tube draining into a collection apparatus.

With the accumulation of biofilm, mineral deposits, or other debris, the connecting tube to the hub of the catheter can be removed to gain access to the tubular isolating medium or material. The tubular isolating medium or material can then be pulled while holding the catheter in place. The act of pulling will draw the portions of the isolating medium or material in contact with body fluids, out of the proximal hub. In removing the soiled, diseased, and/or pathologic portions of isolating medium or material in contact with the body fluids, the same act may also replace those portions of isolating medium or material by drawing upon more tubular isolating medium or material from the reservoir of isolating medium or material located at the proximal hub outside of the inner tube.

Figure 15:
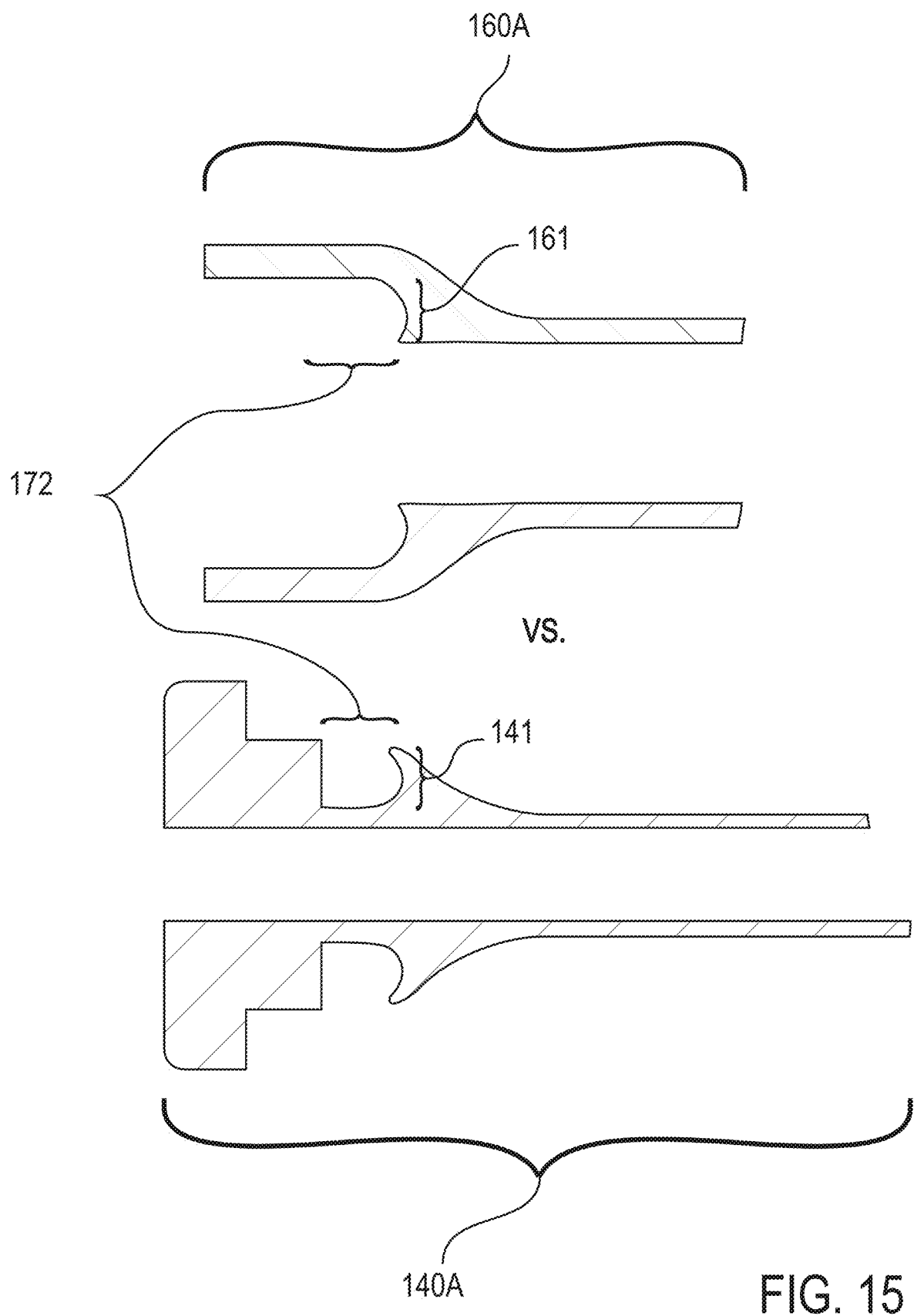
FIG. 15 illustrates a bisected side view of an alternatively geometrically-shaped outer tube as compared to the inner tube, in accordance with at least one embodiment of the invention.

In one aspect, both the inner or outer tubes can be geometrically designed to contain or accommodate an isolating medium or material reservoir as shown by FIG. 15.

Figure 14:
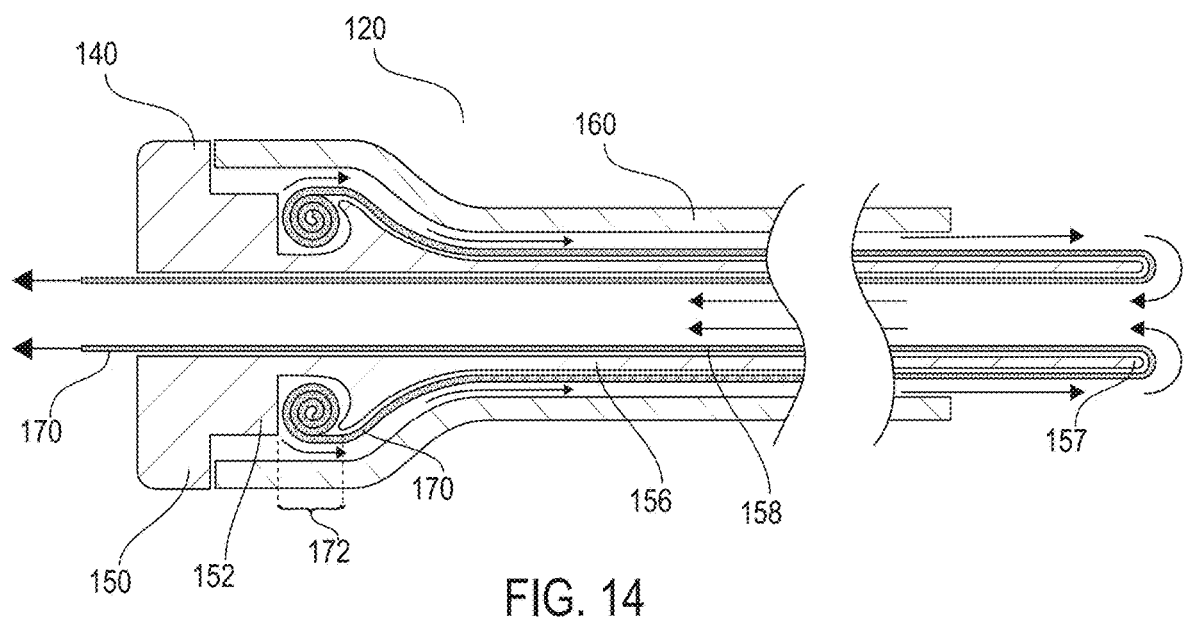
FIG. 14 illustrates a side view of the inner tube of the catheter assembly with a material present in the material reservoir extending down the catheter shaft, in accordance with at least one embodiment of the invention.
Figure 17:
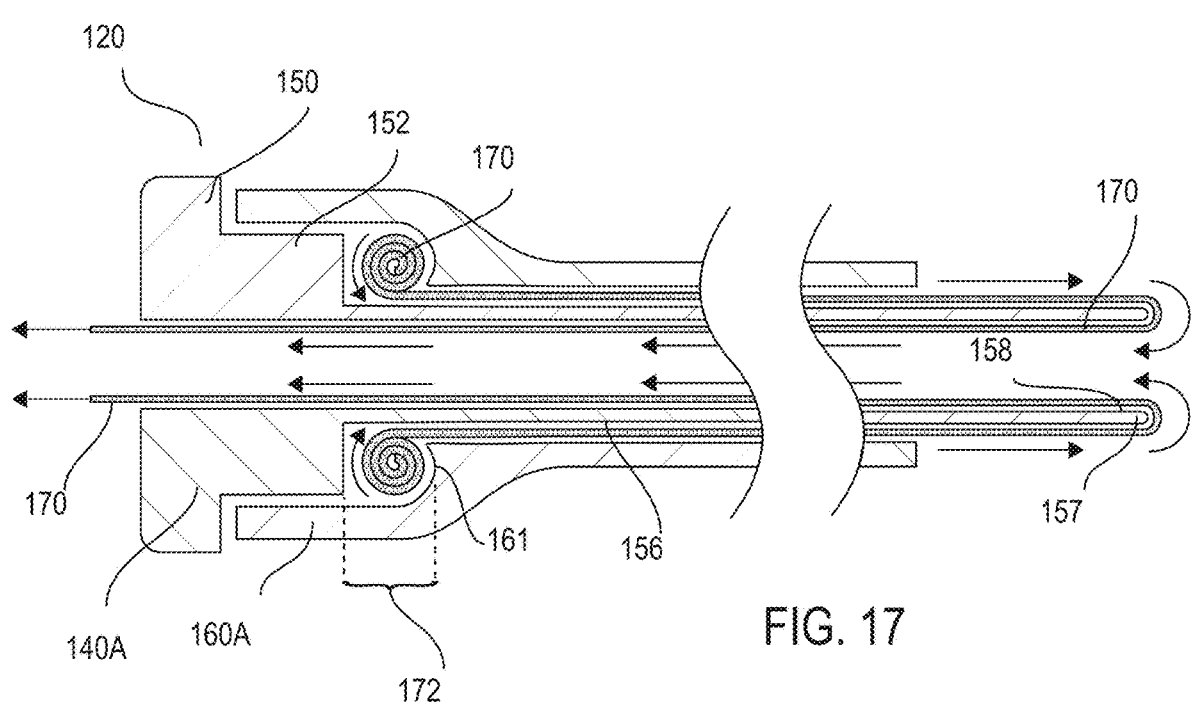
FIG. 17 illustrates a side view of a bisected catheter assembly, in accordance with at least one embodiment of the invention.

In another aspect, the catheter assembly includes an alternative mechanism for film removal via detachable peel-away layers of isolating medium or material. The most proximal portion of each isolating medium or material is adhesed at a point along the inner tube component. By pulling on the corresponding layer at the hub of the draining lumen, the isolating medium or material will detach along the tear line, which connects the isolating medium or material adhesed to a point along the inner tube component and the layer of isolating medium or material that will travel along the direction of arrows as indicated in FIG. 14, and FIG. 17.

Another embodiment of the invention is a catheter assembly comprising or including: an elongated outer tube component having a proximal end and a distal end; an elongated inner tube component having a proximal end and a distal end, and positioned within the elongated outer tube component; and an isolating medium positioned over the elongated inner tube component isolating at least the distal end of the elongated inner tube component from bodily fluids, or other pathological disease. In one aspect, the isolating medium may be a removable isolating medium, for example, a removable isolating medium that is removable through the elongated inner tube component.

In one aspect, the catheter assembly may be a drainage catheter assembly, for example, a renal (kidney) drainage catheter assembly.

In one aspect, the elongated outer tube component and/or the elongated inner tube may include a cavity for the isolating medium.

In one aspect, the catheter assembly may be treatment catheter assembly, for example, fluid treatment of an organ or cavity, such as, a liquid treatment or a gas treatment.

Another embodiment of the invention is a method of introducing or removing a fluid from a body cavity, the method comprising or including: inserting a catheter assembly into a body cavity, the catheter assembly comprising: an elongated outer tube component having a proximal end and a distal end; an elongated inner tube component having a proximal end and an distal end, and positioned within the elongated outer tube component; and an isolating medium positioned over the elongated inner tube component isolating at least the distal end of the elongated inner tube component from bodily fluids; withdrawing a bodily fluid from or introducing a treatment fluid to the body cavity; and removing the isolating medium from at least the distal end of the elongated inner tube component.

In one aspect, the isolating medium may be a first isolating medium, and wherein the method may further include replacing the first isolating medium with a second isolating medium, different from the first isolating medium. For example, the first isolating medium may be connected to the second isolating medium, and replacing the first isolating medium with the second isolating medium may be practiced by extracting the first isolating medium from the catheter assembly and therein drawing the second isolating medium over at least the distal end of the elongated inner tube component.

A further aspect of the invention is an isolating medium for a catheter comprising or including an elongated, flexible, tubular structure having an open first end and an open second end, opposing the first end. In one aspect, the open first end is attachable to a catheter. In another aspect, the isolating medium may be a separable medium, for example, separable from the inner tube component via a connecting mechanism, such as for example, an adhesive or clamping mechanism which joins the isolating medium to the inner tube component when exposed to a predetermined axial tension. The isolating medium may be made of an elastomeric material or a plastic material or other biomaterials. Other materials may be utilized for the isolating medium without departing from this invention.

FIG. 1 is a schematic illustration of a drainage catheter assembly according to one embodiment of the invention. The drainage catheter assembly 120 may be operatively positioned through the skin, kidney cortex, kidney medulla, and into the kidney calyces where the draining lumen lies within the patient's body conduit. FIG. 1. illustrates anatomical overview 100 of a drainage catheter assembly 120 according to one aspect of the invention operatively positioned through skin 102, kidney cortex 103, kidney medulla 104, and into kidney calyces 105, where the draining lumen lies within the patient's body conduit, consisting of either kidney calyces 105, kidney pelvis 106, ureter 107, or bladder 108. The catheter assembly 120 may be connected to a draining apparatus 122 at the proximal end, which may connect to a collecting bag 124 or other receiver. In the example shown, catheter assembly 120 is configured to drain fluid from the kidney collecting system or kidney cavity, which is comprised of kidney calyces 105, and kidney pelvis 106. In other examples, catheter assembly 120 can be configured to administer fluids, chemical agents, or antibiotic solutions to the body cavity (for example, kidney calyces 105, pelvis 106, or body conduit system including the ureter 107 and bladder 108).

When the kidney pelvis 106, ureter 107, or other components of the urinary system are blocked or otherwise compromised, urine cannot naturally drain from the kidney to the bladder 108. Under these conditions, it can be desirable to provide a fluid passage from the kidney cavity through kidney medulla 104, kidney cortex 103, and skin 102 to outside of the body.

A fluid collection reservoir 122, 124 or a fluid applicator can be coupled at a proximal end portion of the catheter assembly 120 such as by way of a hub 126 to gather urine drained from, or inject fluid (for example, medicine) into the kidney cavity.

Figure 2:
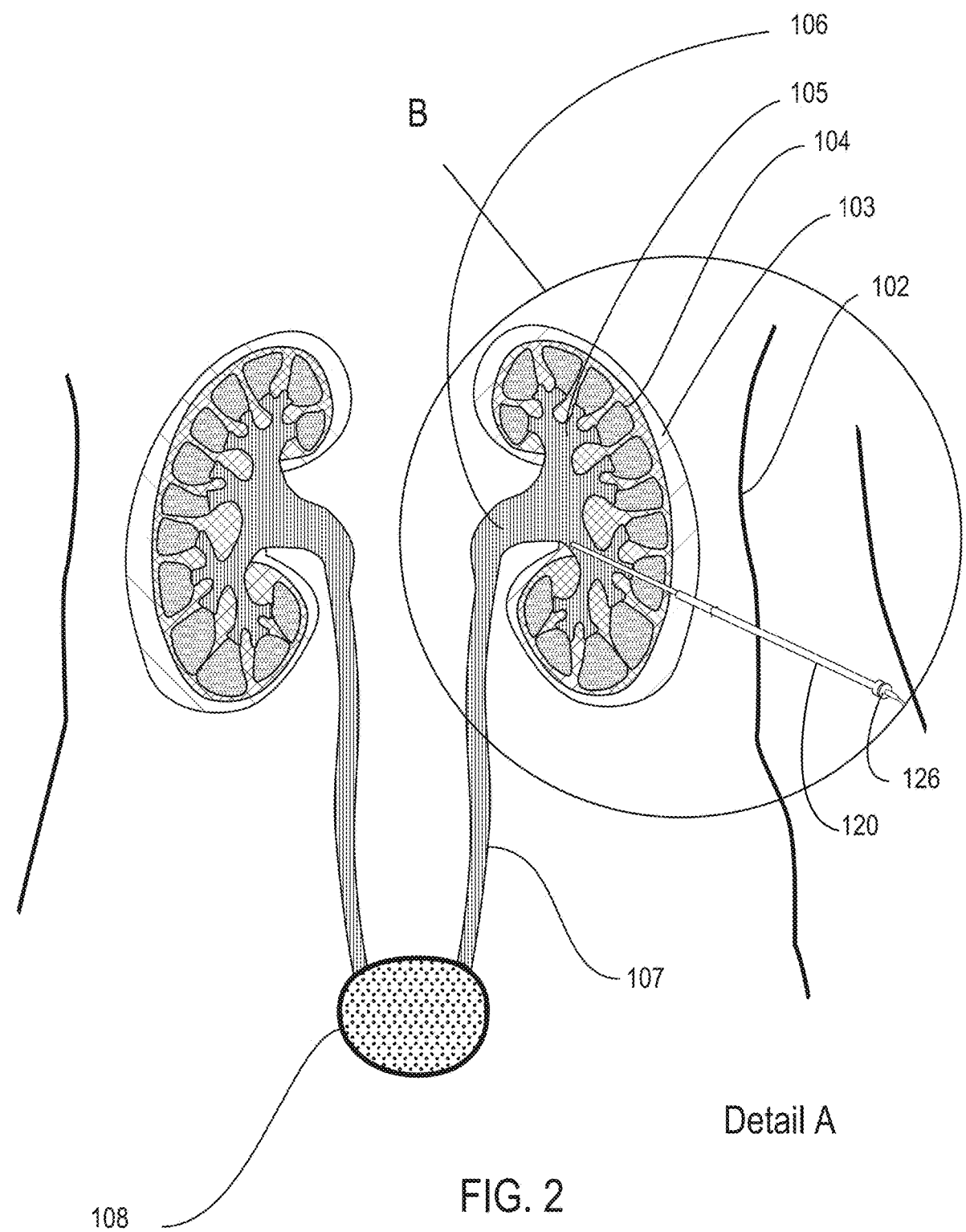
FIG. 2 illustrates detail view A from FIG. 1, which shows portions of the drainage catheter according to one embodiment of the invention.

FIG. 2. illustrates detail view A from FIG. 1 of catheter assembly 120 operatively positioned through the skin 102, kidney cortex 103, kidney medulla 104, and into the kidney calyces 105, where the draining lumen lies within the patient's body conduit, consisting of either the kidney calyces 105, kidney pelvis 106, ureter 107, or bladder 108. Outer tube 124 of the catheter assembly remains within or immediately outside of kidney cortex 103 during both insertion and operation limiting foreign body exposure to the kidney only to the disposable film material which circumferentially covers the draining lumen. The catheter assembly 120 is connected to draining apparatus 122 at proximal end or hub 126.

Though in the following discussion aspects of the invention are shown for withdrawing fluid or treating a kidney, it is envisioned that aspects of the invention may be used for extracting fluid or gas and/or treating any bodily organ or bodily cavity, both for human and animal patients. For example, other cavities or organs that can be accessed by aspects of the invention include but are not limited to the gall bladder, bladder, abscess collections, pancreas, cysts, pseudocysts, abdominal cavity, thoracic cavity, or the pleural space. The invention may also be applied in assistive ventilator devices including but not limited to laryngeal tubes, tracheal tubes, or intubation applications.

Figure 3:
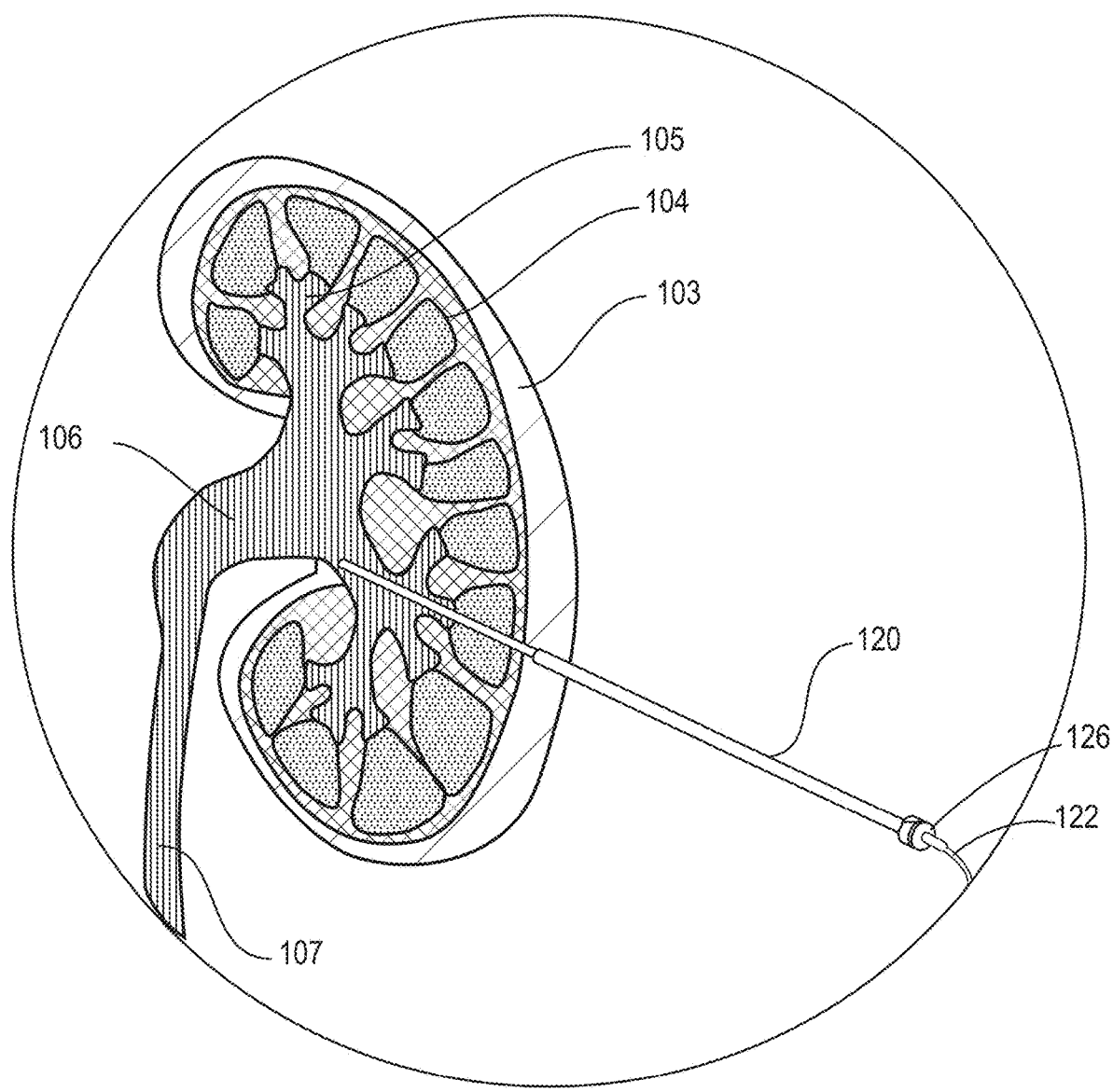
FIG. 3 illustrates detail view B from FIG. 2, which shows portions of the drainage catheter assembly according to one embodiment of the invention.

FIG. 3. illustrates detail view B of catheter assembly 120 from FIG. 2 operatively positioned through the kidney cortex 103, kidney medulla 104, and into the kidney calyces 105, where the draining lumen lies within the patient's body conduit, consisting of either the kidney calyces 105, kidney pelvis 106, or ureter 107. Catheter assembly 120 is connected to a draining apparatus 122 at the proximal end or hub 126, which connects to a collecting bag 124.

Figure 4:
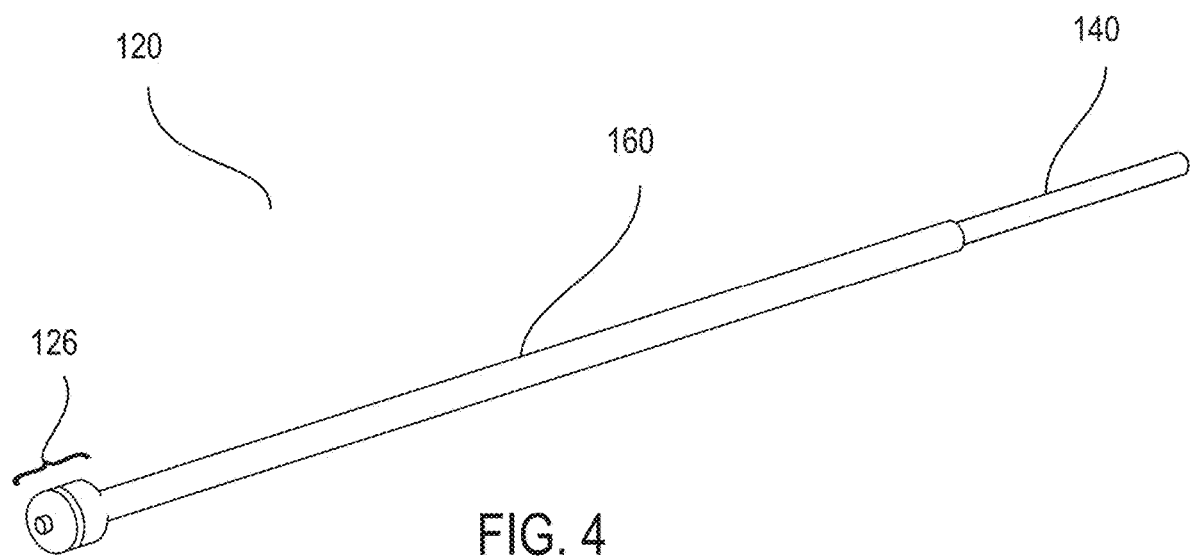
FIG. 4 illustrates an isometric view of the inner tube component of the catheter assembly, in accordance with at least one embodiment of the invention.
Figure 6:
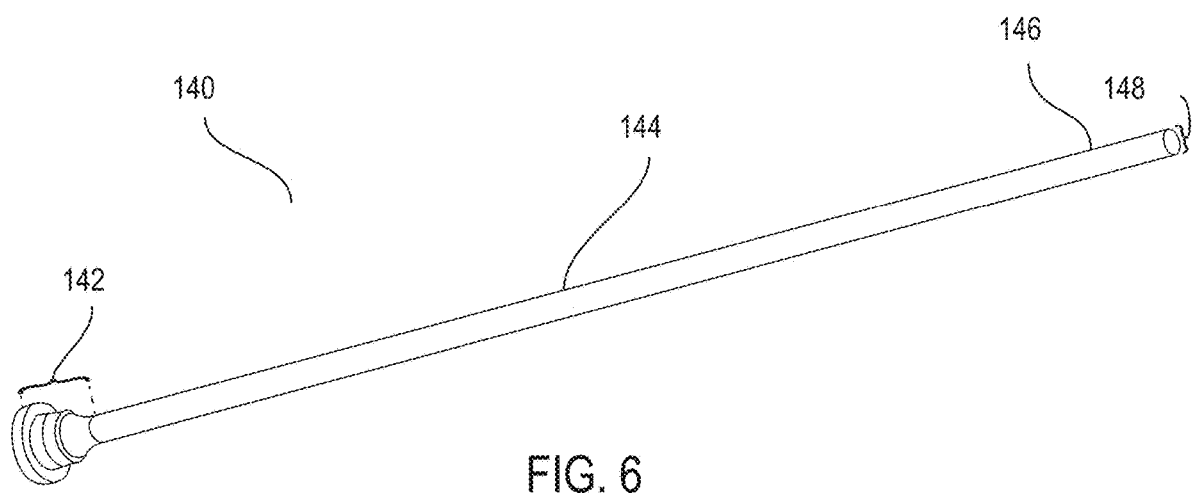
FIG. 6 illustrates an isometric view of the catheter assembly, in accordance with at least one embodiment of the invention.
Figure 7:
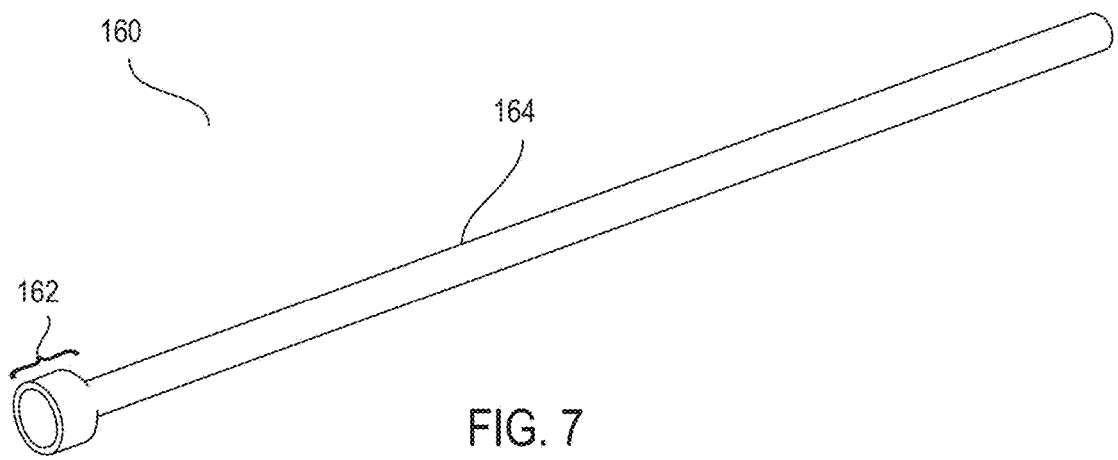
FIG. 7 illustrates an isometric view of the catheter assembly, in accordance with at least one embodiment of the invention.

FIG. 4 illustrates the catheter assembly 120 shown in FIGS. 1 through 3 comprised of the outer tube component 160 shown in FIG. 7 connected over the inner tube component 140 shown in FIG. 6. The outer tube component 160 and inner tube component 140 are connected at the catheter assembly hub 126.

Figure 5:
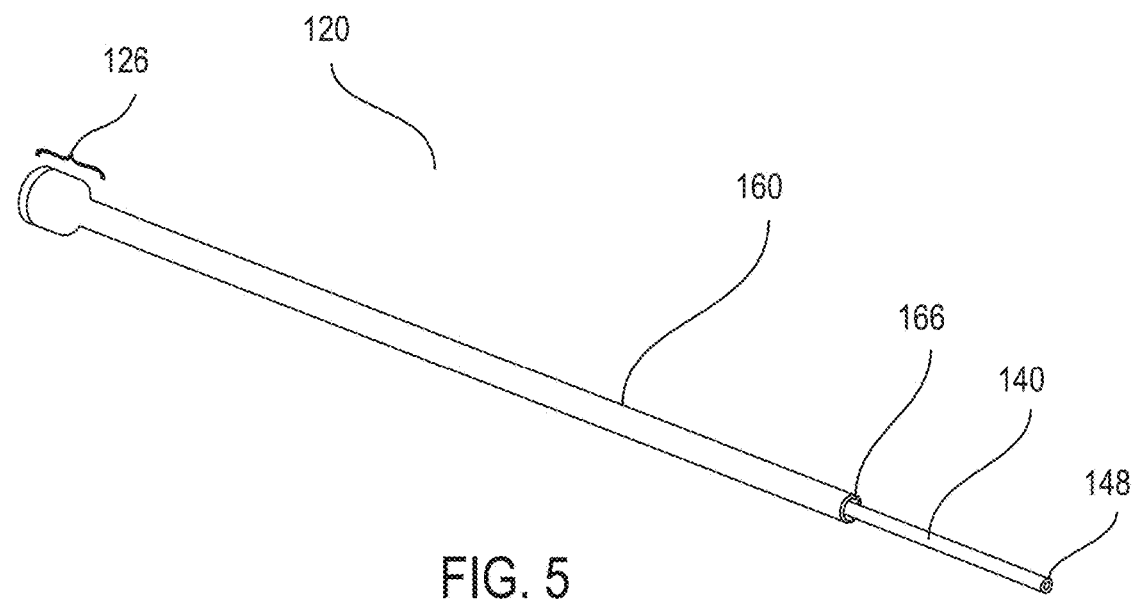
FIG. 5 illustrates an isometric view of the outer tube component of the catheter assembly, in accordance with at least one embodiment of the invention.

FIG. 5 illustrates the catheter assembly 120 comprised of the outer tube component 160 connected over the inner tube component 140. The outer tube component 160 and inner tube component 140 are connected at the catheter assembly hub 126. The interspace 166 is the space between the outer tube component 160 and inner tube component 140 through which a tubular material will travel through before inverting and entering the inner tube lumen 148.

FIG. 6 illustrates the inner tube component 140 of the catheter assembly 120 shown in FIGS. 1 through 3 shown with the proximal hub 142, inner tube shaft 144, and inner tube tip 146, which forms the outer rim 148 of the inner tube lumen. The inner tube component 140 connects to the outer tube component 160 to form the catheter assembly 120.

FIG. 7 illustrates the outer tube component 160 of the catheter assembly 120 shown in FIGS. 1 through 3 shown with the proximal hub 162, outer tube shaft 164. The outer tube component 160 connects over the inner tube component 140 to form the catheter assembly 120.

Figure 8:
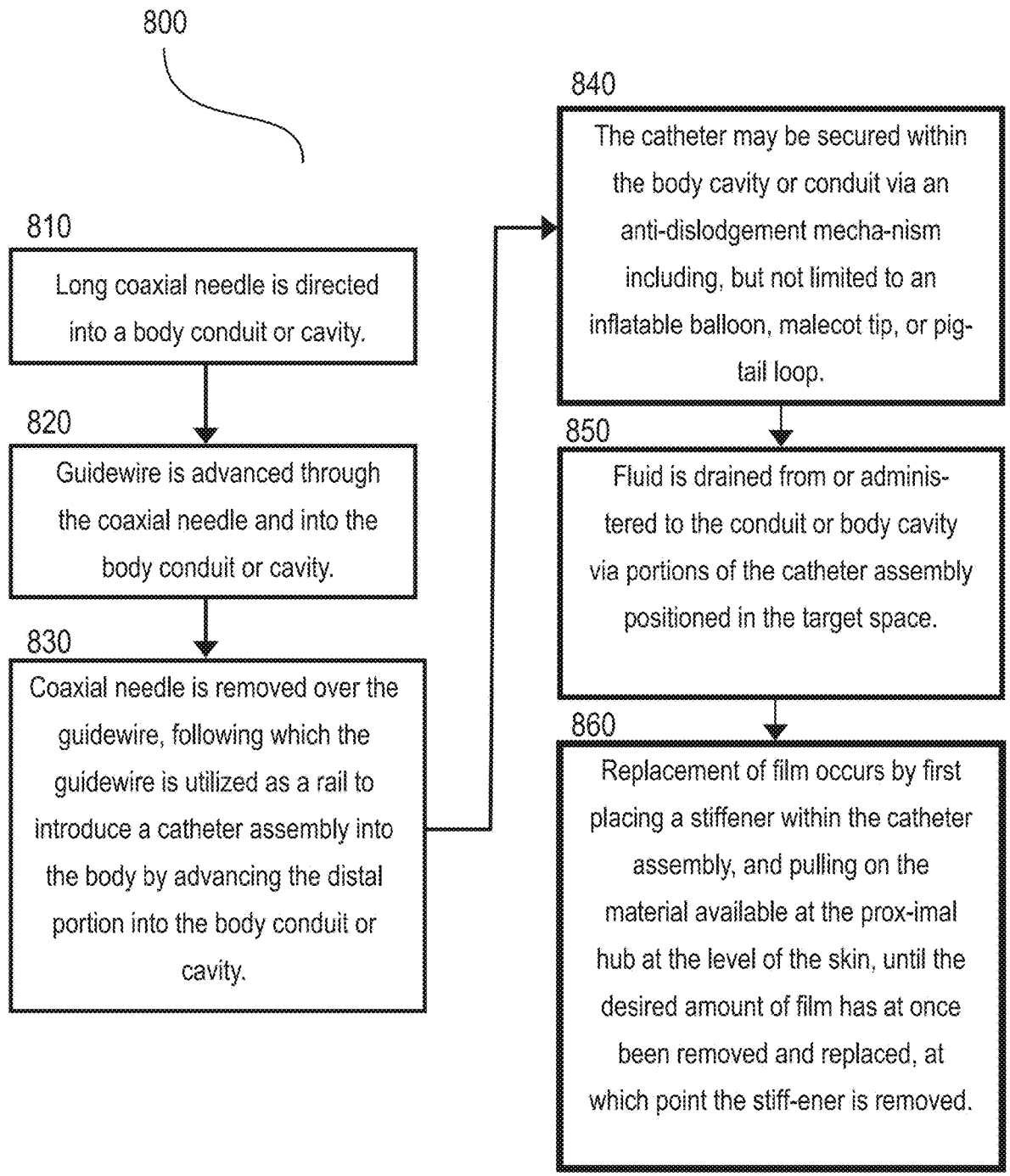
FIG. 8 illustrates an example method of using the catheter assembly, in accordance with at least one embodiment of the invention.

FIG. 8 illustrates a flow chart of an example method 800 of using the catheter assembly 120, as conceived by the present inventor. In operation 810, a long coaxial needle is directed into a body conduit or cavity. In operation 820, a guidewire is advanced through the previously inserted coaxial needle and into the same body cavity or conduit. With the guidewire in place, the coaxial needle is removed over the guidewire, following which the guidewire is utilized as a rail to introduce a catheter assembly 120 into the body by advancing the distal portion of catheter assembly 120 into the body conduit or cavity in operation 830. At this point, the catheter assembly 120 may be secured within the body cavity or conduit via an anti-dislodgement mechanism including, but not limited, to an inflatable balloon, Malecot tip, or pig-tail loop in operation 840. In operation 850, the placed catheter assembly 120 can drain or administer fluid via portions of the catheter assembly 120 positioned within the body conduit, body cavity, or target space. In operation 860, replacement of the isolating medium or film may occur by first placing a stiffener within the catheter assembly 120, pulling on the material available at the proximal hub, and pulling until the desired amount of isolating medium or film has at once been removed and replaced, at which point the stiffener is removed.

Figure 9:
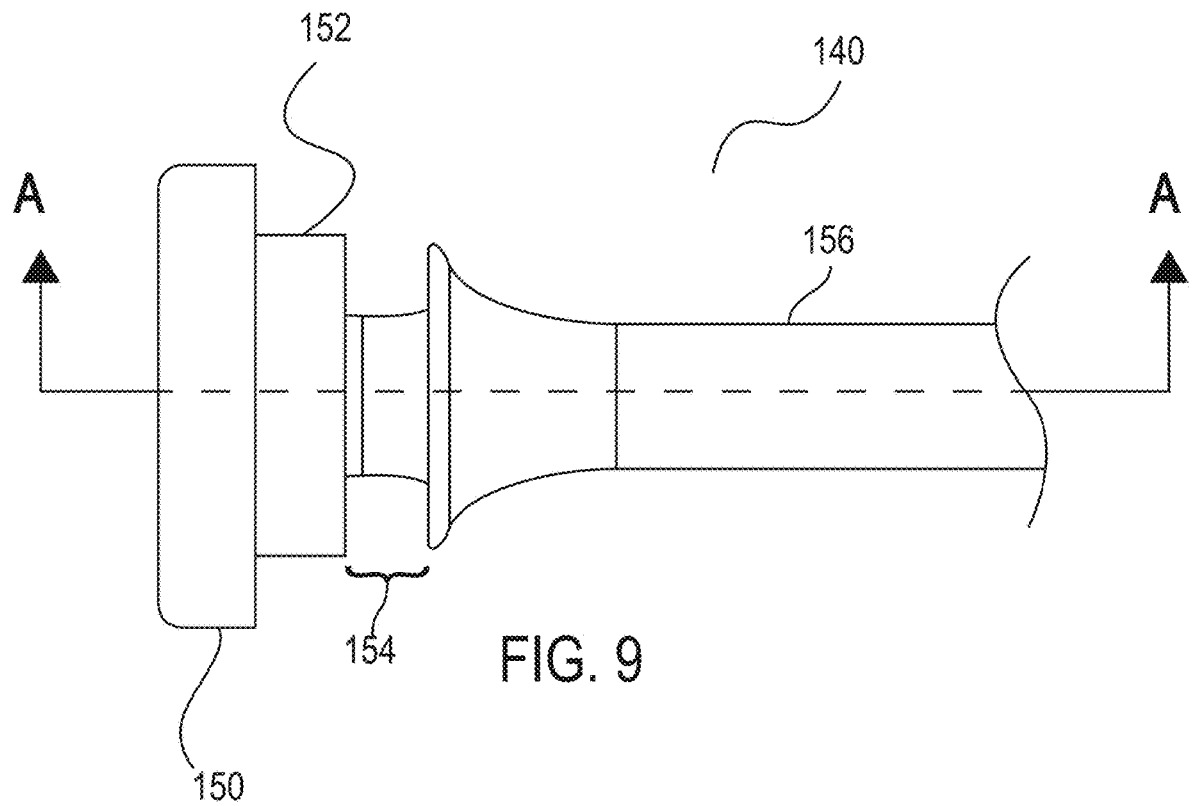
FIG. 9 illustrates a side view of the inner tube of the catheter assembly, in accordance with at least one embodiment of the invention.

FIG. 9 illustrates a side-view of the proximal portion of the inner tube component 140 of the catheter assembly 120 shown in FIGS. 4 through 7. The present inventor recognizes that with existing catheter assemblies, occlusion of the draining lumen by biofilm, debris, or encrustation may prevent adequate draining of the fluid space or adequate filling of injected material. In prior art devices, when blockage or obstruction of the draining lumen occurs, patients can be subject to various complications, including but not limited to, kidney infection, sepsis, and permanent kidney damage. In order to avoid these complications, in the prior art, catheter exchanges or repeat placements occur.

To help minimize debris, biofilm accumulation, or mineral encrustation from causing blockage of the catheter, in one aspect, the catheter assembly 120 isolates the catheter from the urine or fluid environment otherwise, by an isolating medium 170, for example, a film, such as, a disposable film, which covers, surrounds, or envelops the fluid-exposed portions of the catheter assembly 120. The film 170 may be contained atop the inner tube component 140, which, as shown in FIG. 9, may include a flange 150, a fastener system 152, a material reservoir 154, and an inner tube shaft 156. The flange 150 may function as a surface against which the outer tube component 160 of catheter assembly 120 may engage. The fastener system 152 may complement a fastener system (not shown) on the outer tube component 160 of catheter assembly 120 to form a locking mechanism. The locking mechanism may operate such that the inner tube component 140 and outer tube component 160 engage to form catheter assembly 120. The locking mechanism may be a variety of mechanism such that the hub of the inner tube component 140 can be connected to the outer tube component 160. The locking mechanism may be a lock and key mechanism between the inner tube component 140 and the outer tube component 160. The locking mechanism may also be a screw connector between the inner tube component 140 and the outer tube component 160. In another embodiment, the inner tube component 140 and the outer tube component 160 may be a single piece without a need for a locking mechanism. The isolating medium 170 may be contained within the material reservoir 154, from which the isolating medium 170 may extend along the outer surface of the inner tube component 140, for example, extend along the inner tube shaft 156.

Figure 10:
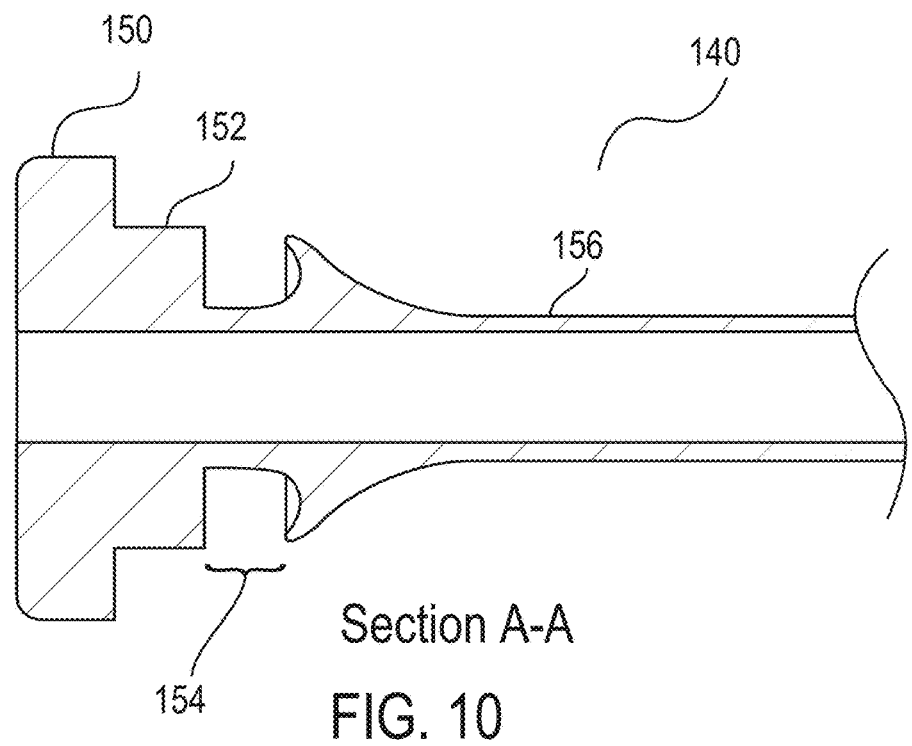
FIG. 10 illustrates a cross-sectional side view of the inner tube of the catheter assembly, in accordance with at least one embodiment of the invention.

FIG. 10 illustrates a cross-sectional view of the inner tube component 140 of catheter assembly 120 as viewed allow section lines A-A in FIG. 9. This cross-sectional view shows the flange 150, the fastener system 152, the material reservoir 154, and the inner tube shaft 156.

Figure 11:
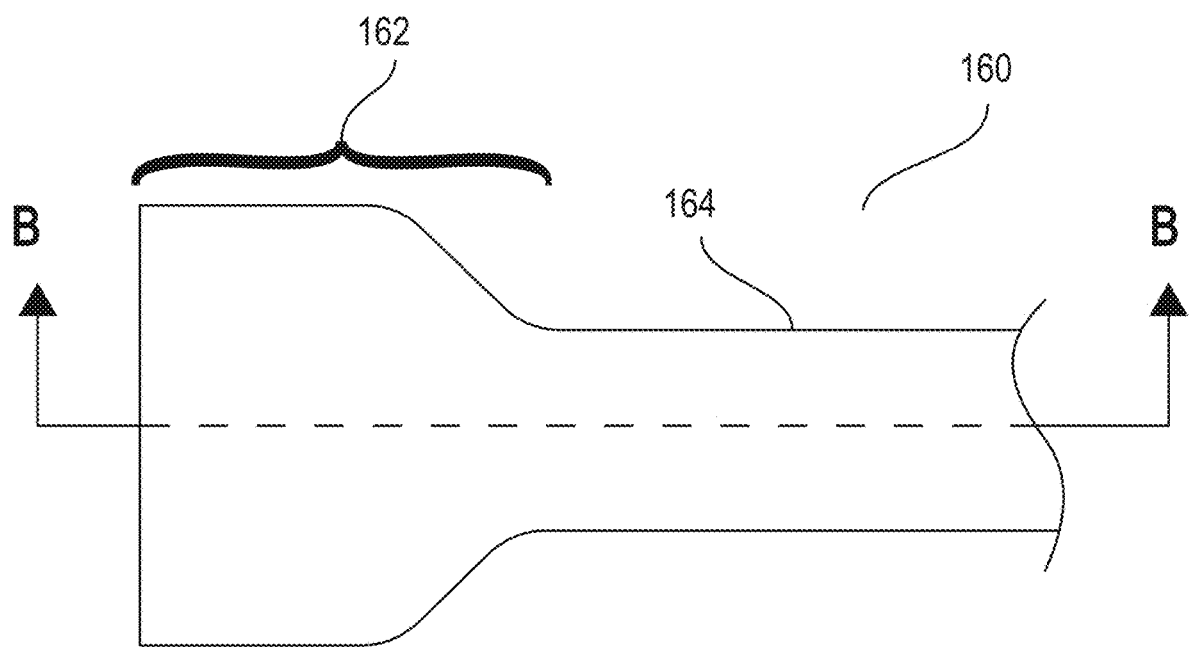
FIG. 11 illustrates a side view of the outer tube of the catheter assembly, in accordance with at least one embodiment of the invention.

FIG. 11 illustrates a side view outer tube component 160 of the catheter assembly 120 shown in FIGS. 4 through 7. The outer tube component 160 is composed of a hub 162, which connects to the inner tube component 140 via a fastening mechanism to attach or secure the inner tube component 140 and to the outer tube component 160, and a shaft 164. Distal to the hub 162, the shaft 164 elongates distally.

Figure 12:
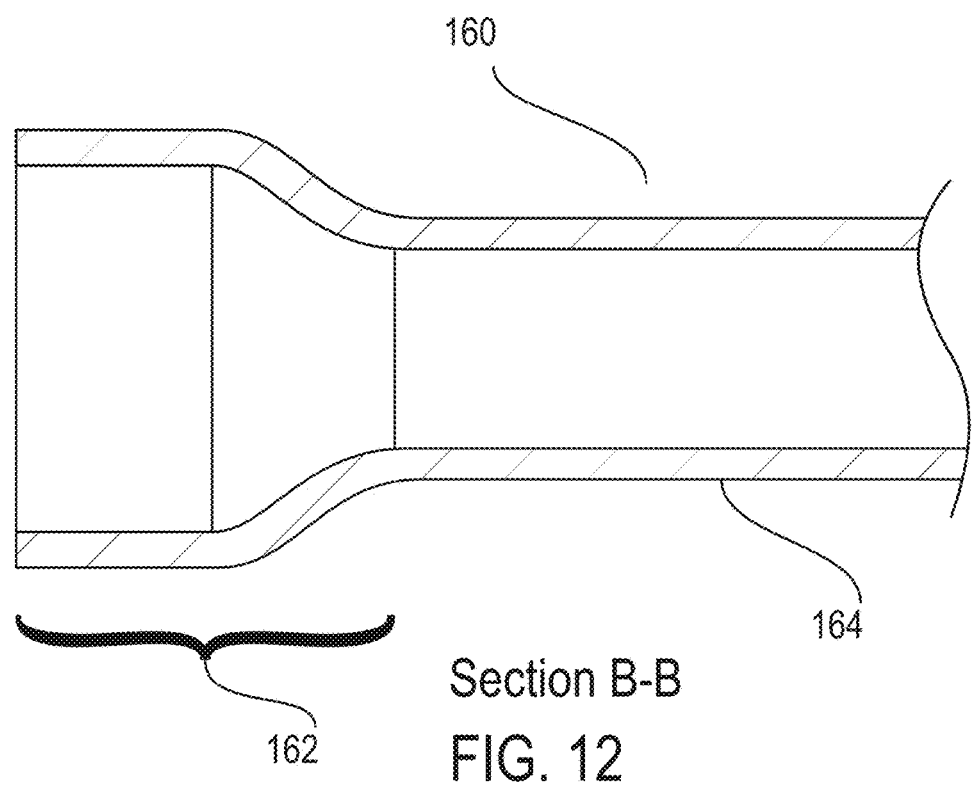
FIG. 12 illustrates a side view of a bisected outer tube, of the catheter assembly, in accordance with at least one embodiment of the invention.

FIG. 12 illustrates a cross-sectional view of the outer tube component 160 of catheter assembly 120 as viewed allow section lines B-B in FIG. 11. As shown, outer tube component 160 includes hub 162, which connects to inner tube component 140 via a fastening mechanism to attach or secure the inner tube component 140 and outer component 500, and a shaft 164. Distal to hub 162, the shaft 164 elongates distally.

Figure 13:
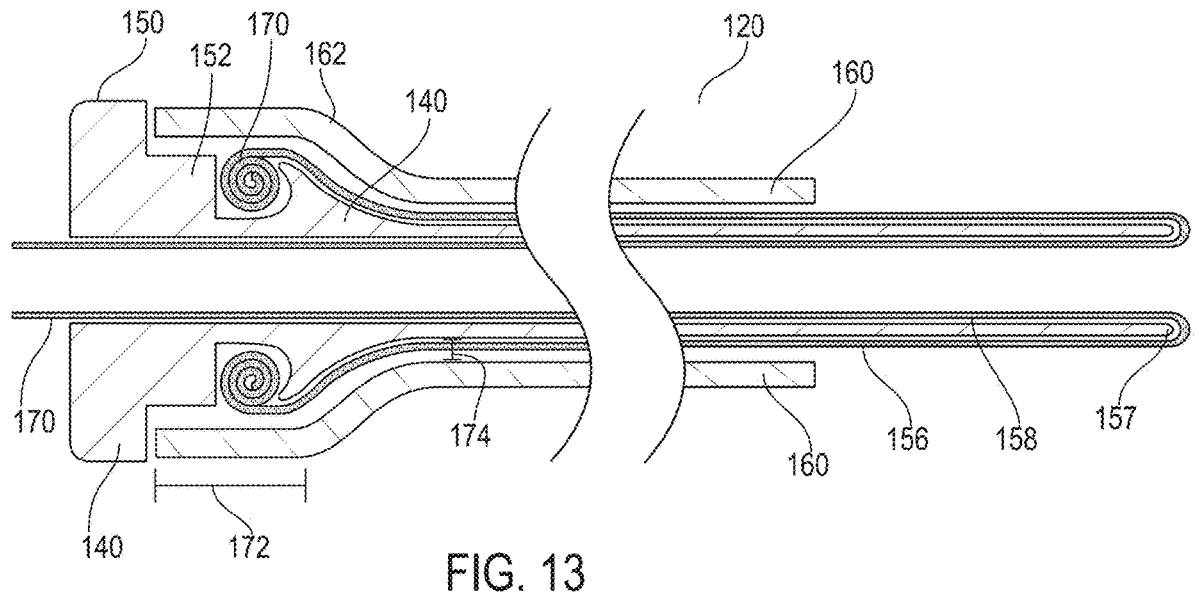
FIG. 13 illustrates a side view of a bisected inner tube, outer tube, and the material coursing from the material reservoir through the space between the inner and outer tube of the catheter assembly, in accordance with at least one embodiment of the invention.

FIG. 13 illustrates a cross-sectional view of catheter assembly 120 shown in FIGS. 4 through 7. According to an aspect of the invention, catheter assembly 120 includes inner tube component 140, outer tube component 160, and isolating medium 170. Isolating medium 170 may be retained in and extend from material reservoir 172 through a space, for example, an annular space, between the inner tube component 140, and outer tube component 160 of catheter assembly 120, forms a channel 174. The outer tube component 160 and the inner tube component 140 may interface, engage, or contact at the flange 150, with a fastening system 152 adjacent to it, connecting the inner tube component 140 and the outer tube component 160 as one catheter assembly 120. The isolating medium 170 may be configured into a tubular roll, finger-cot configuration, or other geometrically accommodating shape. The isolating medium 170 may be held, stored, or retained within material reservoir 172. The space between the inner tube component 140 and outer tube component 160 forms channel 174 for isolating medium 170. Through this channel 174, the isolating medium 170 on the outer diameter of the inner tube 156 travels down and covers the inner tube shaft 156, before inverting along the distal tip of the inner tube 157 to form an isolating medium or material on the inner diameter of the inner tube 158. The isolating medium 170 or material courses from the distal to proximal portion of the inner diameter of the inner tube 158, before the isolating medium 170 or material extends beyond catheter assembly 120.

FIG. 14 illustrates a cross-sectional view of catheter assembly 120 with isolating medium or material 170 present in the material reservoir extending down the catheter shaft with directional arrows delineating a potential path of travel. Adjacent to the flange 150 and fastener system 152, inner tube of catheter assembly 120 has a material reservoir 172 geometrically shaped to hold a tubular isolating medium or material on the outer diameter of the inner tube component 140. This isolating medium or material 170 travels down and covers the inner tube shaft 156, before inverting its direction of travel along the distal tip 157 to extend down the inner diameter 158 of the inner tube component 140. The material continues to course down the inner diameter 158 of the inner tube component 140 of the catheter assembly 120 before the isolating medium or material 170 extends beyond the catheter assembly 120.

FIG. 15 illustrates a cross-sectional view of an alternatively geometrically-shaped outer tube component 160A and inner tube component 140A. In a catheter assembly 120, the reservoir space 172 may be limited by the geometric shape of either the inner tube component 140A or the outer tube component 160A. The outer tube circular abutment 161 as compared to the inner tube circular abutment 141, differ in their position on either the outer tube component 160A or the inner tube component 140A, but serve to accommodate isolating medium 170 contained within material reservoir 172.

Figure 16:
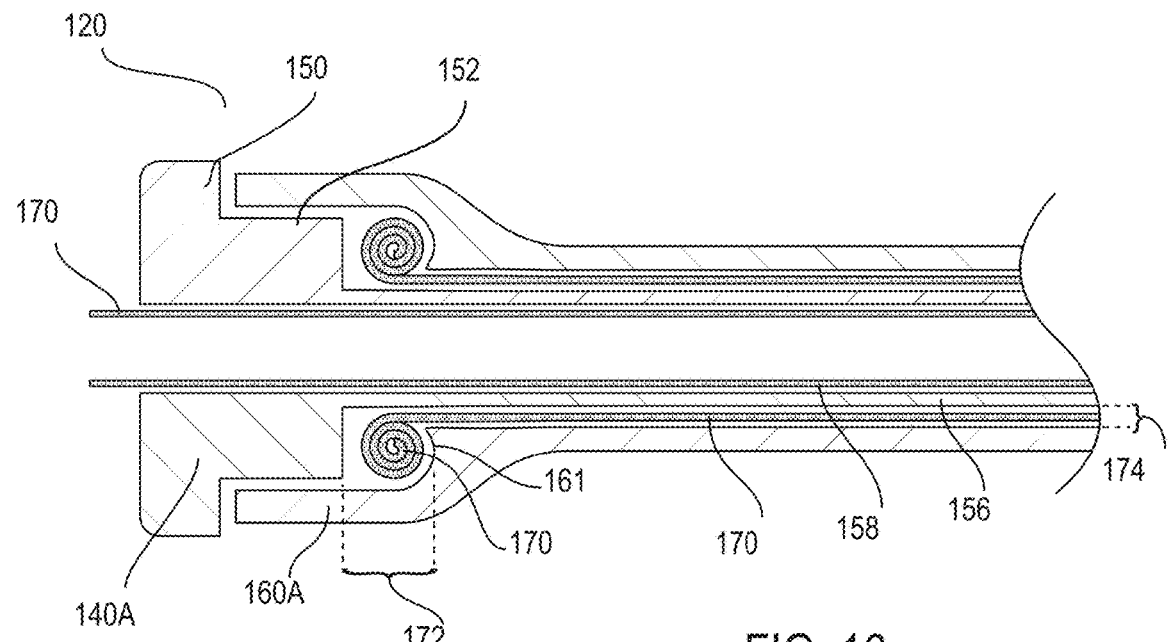
FIG. 16 illustrates a side view of a bisected catheter assembly, in accordance with at least one embodiment of the invention.

FIG. 16 illustrates a cross sectional view of catheter assembly 120 comprised of an inner tube component 140A, alternatively geometrically-shaped outer tube component 160A, and isolating medium or material 170 coursing from the material reservoir 172 through the space between the inner tube component 140A and outer tube component 160A of the catheter assembly 120. The outer tube component 160A and inner tube component 140A engage at flange 150, with fastening system 152 adjacent to it, engaging the inner tube component 140A and outer tube component 160A as one assembly. The isolating medium or material 170, configured into a tubular roll, finger-cot configuration, or other geometrically accommodating shape, is held within material reservoir 172, and circular abutment 161 on the outer tube component 160A accommodates isolating medium or material 170 contained within the material reservoir 172. The space between inner tube component 140A and outer tube component 160A forms material channel 174. Through material channel 174, the isolating medium or material 170 on outer diameter of the inner tube component 140A travels down and covers the inner tube shaft 156, before inverting along distal tip 157 of inner tube component 140A to extend insolating medium or material 170 on inner diameter 158 of the inner tube component 140A. The isolating medium or material 170 courses from the distal to proximal portion of the inner diameter 158 of the inner tube component 140A, before isolating medium or material 170 extends beyond the catheter assembly 120.

FIG. 17 illustrates a cross-sectional view of catheter assembly 120 comprised of inner tube component 140A, alternatively geometrically-shaped outer tube component 160A, and isolating medium or material 170 coursing throughout the catheter assembly 120 with arrows to denote the directionality of the material 170 course as it is pulled from the proximal end of the catheter. Adjacent to the flange 150 and fastener system 152, inner tube component 140A of the catheter assembly 120 has a material reservoir 172 that is accommodated to hold isolating medium or material 170 on outer diameter of the inner tube component 140A by the alternatively geometrically-shaped outer tube component 160A, and its outer tube abutment 161. Isolating medium or material 170 travels down and covers the inner tube shaft 156, before inverting its direction of travel along the distal tip 157 to extend isolating medium or material 170 on inner diameter 158 of inner tube component 140A. This material 170 continues to course down inner diameter 158 of inner tube component 140A before the isolating medium or material 170 extends beyond catheter assembly 120.

Figure 18:
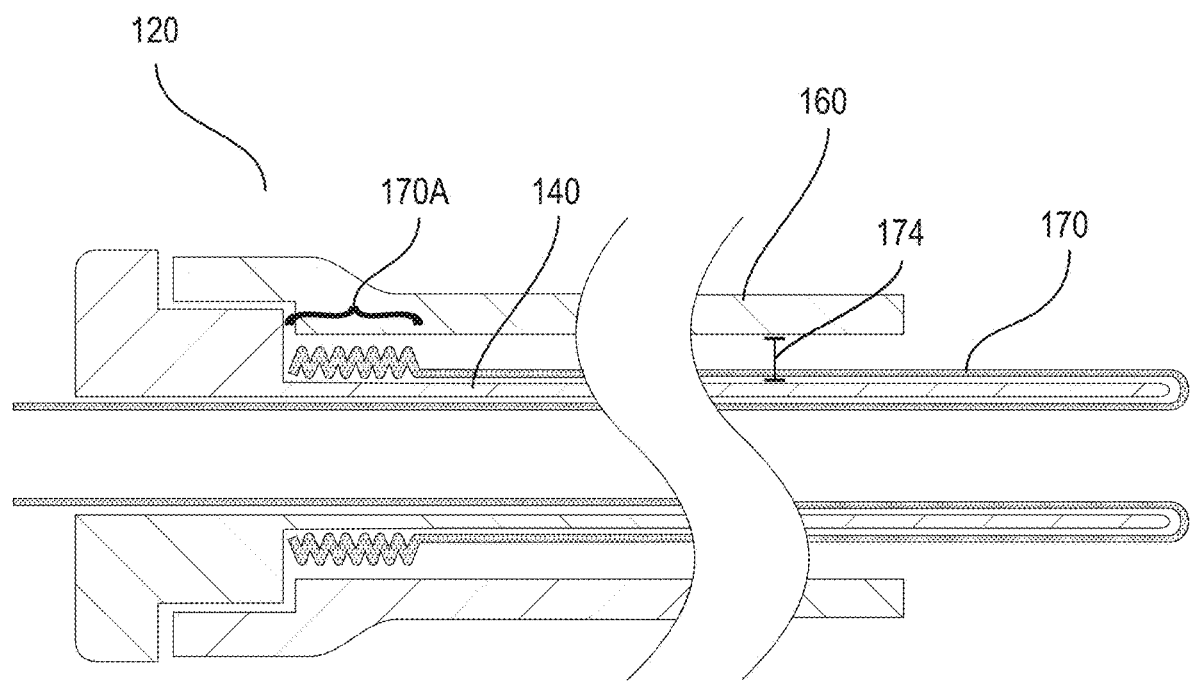
FIG. 18 illustrates another embodiment of the catheter assembly, in accordance with at least one embodiment of the invention.

FIG. 18 illustrates one possible alternative embodiment where the disposable film 170, or isolating medium or material 170, is stored by compressing the film 170 along outer circumference of inner tube component 140 in the proximal direction of the axis of the tube as depicted by callout 170A. The mechanism by which the disposable film 170 is removed and replaced is similar to that of the mechanisms described in the aforementioned FIGS. 14 and 17.

Figure 19:
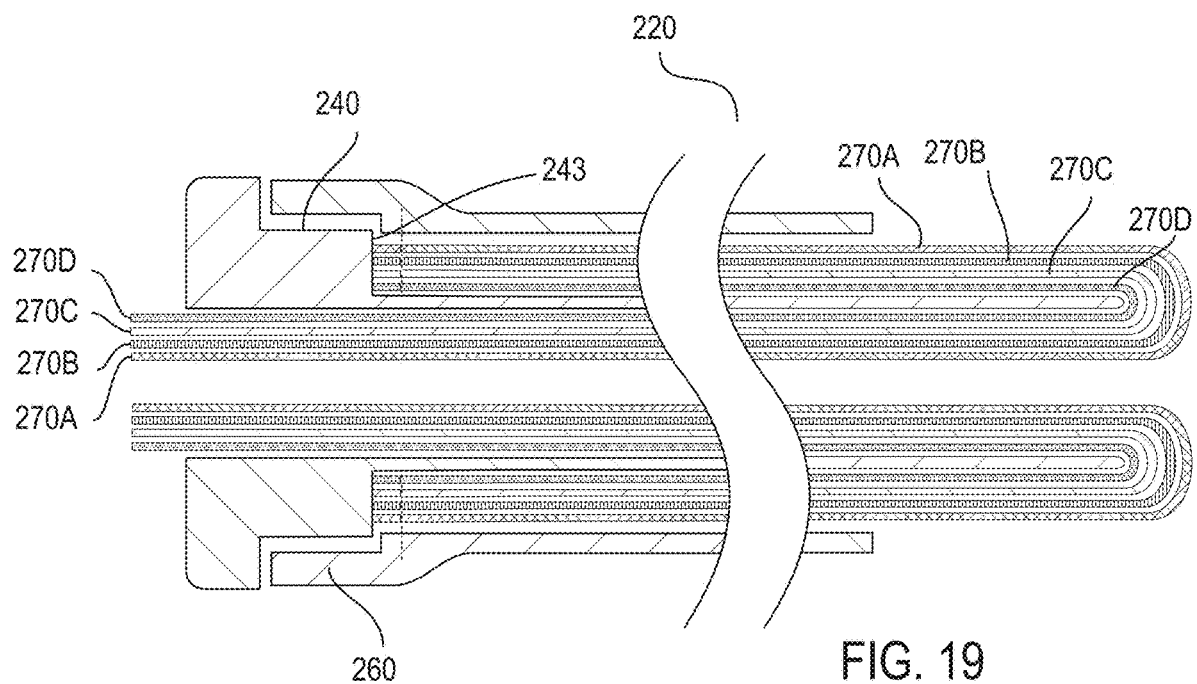
FIG. 19 illustrates another embodiment of the catheter assembly, in accordance with at least one embodiment of the invention.

FIG. 19 illustrates one possible alternative mechanism for a catheter assembly 220 of operation for replacing the tubular isolating medium or material 270A, 270B, 270C, 270D. For the embodiments regarding the catheter assembly 220, the features are referred to using similar reference numerals under the "2xx" series of reference numerals, rather than "1xx" as used in the previous embodiments. Accordingly, certain features of the catheter assembly 220 that were already described above with respect to the catheter assembly 120 may be described in lesser detail, or may not be described at all. The tubular isolating medium or material 270A, 270B, 270C, 270D which circumferentially covers the inner tube component 240 of the catheter assembly 220. Catheter assembly 220 differs in the mechanism by which the disposable film which covers the draining lumen is replaced by new and unsoiled disposable material, however, is similar in construction to the catheter assembly embodiments previously described within this document. According to this aspect, the isolating medium or material 270A, 270B, 270C, 270D is layered in separate tubular sheets of disposable film material connected at any point along the inner tube component 240 via some connecting mechanism 243, such as for example, an adhesive or clamping mechanism which joins disposable film 270A, 270B, 270C, 270D to the inner tube component 240. For example, in one aspect, the separate disposable, tubular sheets of isolating medium may overlay each other and be separately removed when, for example, soiled. It should be noted that the aforementioned connecting mechanism 243 can also be made to connect the disposable film 270A, 270B, 270C, 270D to the outer tube component 260 of catheter assembly 220 in alternative embodiments.

Figure 20:
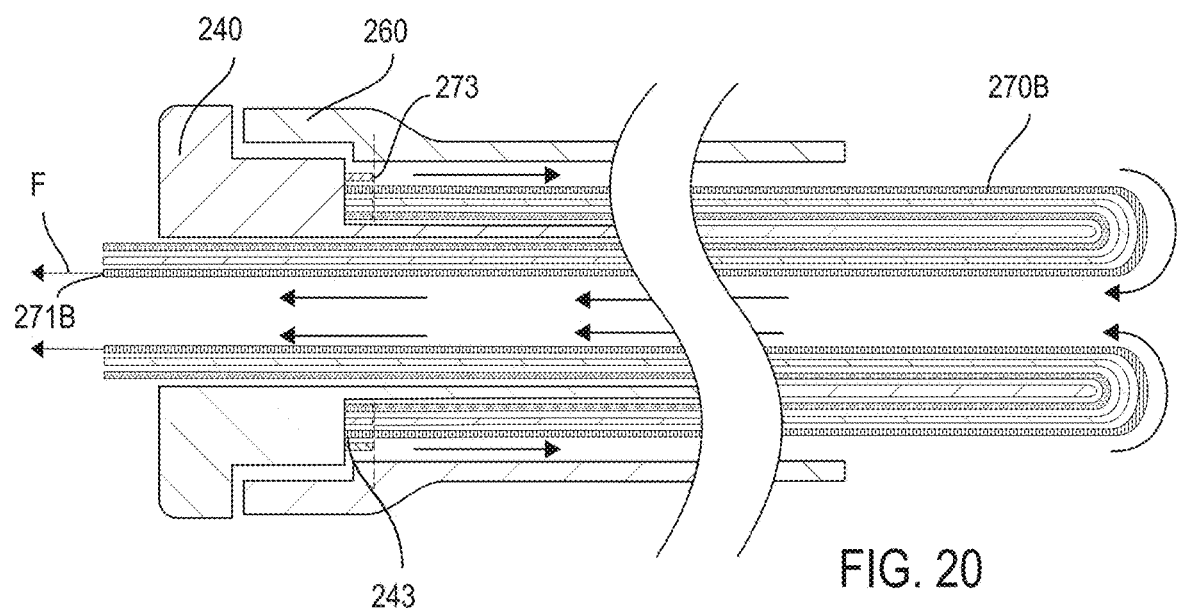
FIGS. 20-22 illustrate the mechanism of the catheter assembly as illustrated in FIG. 19, in accordance with at least one embodiment of the invention.
Figure 21:
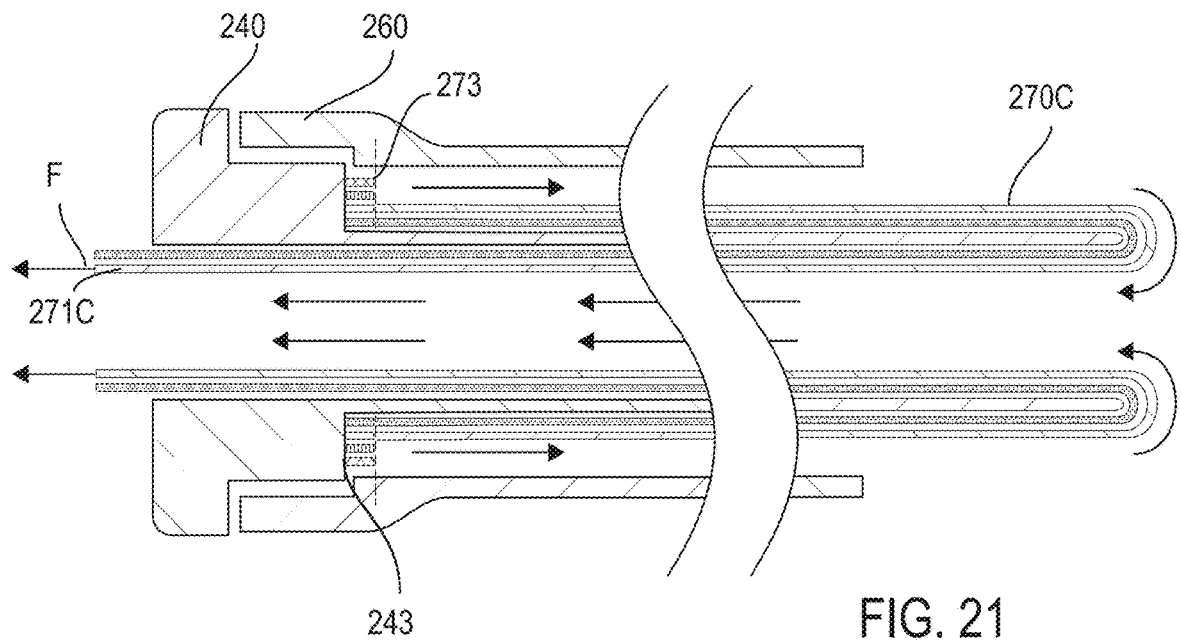
Figure 22:
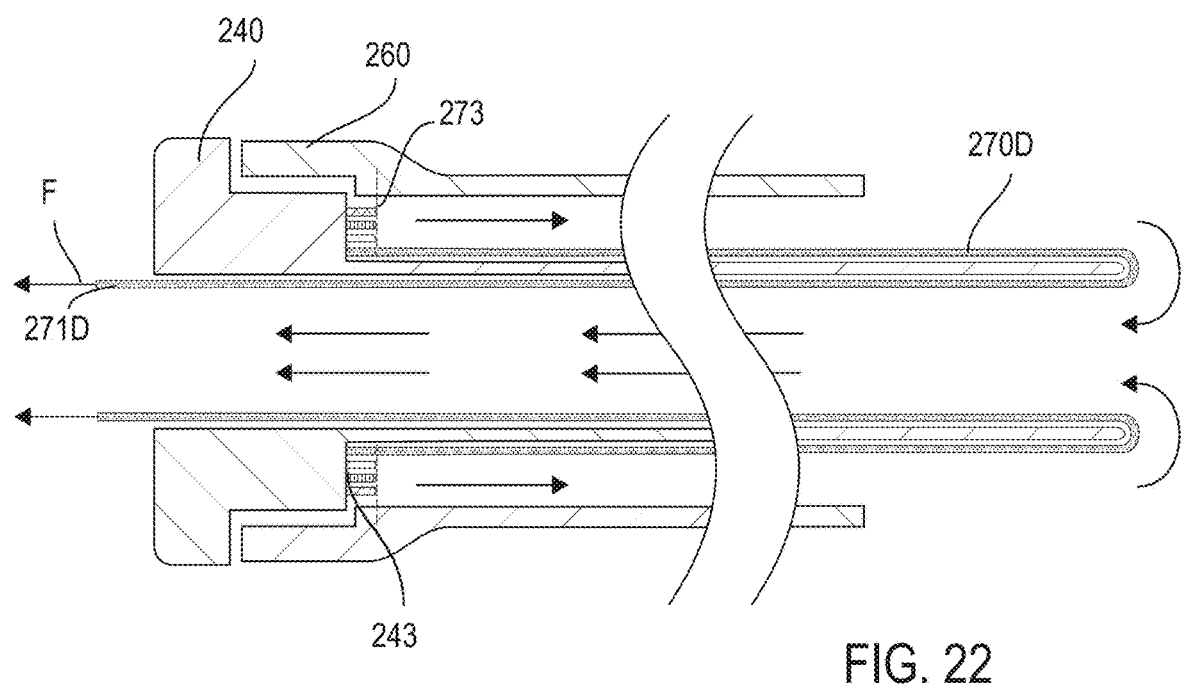

FIGS. 20, 21, and 22 illustrate the mechanism by which the embodiment of the catheter assembly 220 previously described in FIG. 19 where separate sheets of isolating medium 270A, 270B, 270C, 270D can be removed to expose an unsoiled replacement sheet, which covers the inner tube component 240 with new and unsoiled disposable film material. FIGS. 20, 21, and 22 are arranged in numerically sequential fashion where FIG. 20 represents the first figure in the sequence and FIG. 22 represents the last figure in the sequence.

Catheter assembly 220 accomplishes the novel method of replacing the disposable film material 270A, 270B, 270C, 270D with new and unsoiled disposable film material by allowing the film material 270A, 270B, 270C, 270D to be pulled by some force F at the proximal end of the catheter assembly 220. As this force F is applied to the proximal terminating end 271B of the disposable tubular film material 270A the resultant force causes film material 270A to break off from connecting mechanism 243 allowing for the undesired film material 270A to travel from the proximal end to the distal end of catheter assembly 220 where it then inverts its direction of travel at the most distal end of catheter assembly 220 and continues to travel through the inner draining lumen of inner tube component 240 from the distal to the proximal end and finally out of the catheter assembly 220 as denoted by the arrows in FIGS. 20, 21, and 22. The point of location of film material disconnection 273 can be precisely engineered during the disposable film manufacturing process, such as for example, creating a perforation in the disposable film 270A, 270B, 270C, 270D at the point of location of the film material disconnection 273. It should be noted that other methods of disconnecting the film material 270A, 270B, 270C, 270D from connecting mechanism 243 are possible in other embodiments, such as but not limited to, cutting, melting, or the release of some clamping mechanism.

After the process of removing film layer 270A from the catheter assembly 2000, film layer 270B now becomes the new and unsoiled layer of disposable film material which is exposed to the body effectively accomplishing the task of removing and replacing the drainage catheter with a new and unsoiled material eliminating the need to completely change a drainage catheter inside a person. This process can be repeated a number of times which is equivalent to the quantity of layers of disposable material contained within catheter assembly 220. It should be noted that the embodiment illustrated by FIGS. 19, 20, 21, and 22 contains four layers of disposable film material, however, at least two layers, or at least three layers, or any number of layers can be used in alternative embodiments.

FIGS. 23 and 24 illustrate the geometry and relative size of the isolating material medium 170 as they relate to catheter assembly 120. Section C-C of FIG. 23 illustrates a cross-sectional view of one possible embodiment of tubular isolating medium 170. Section D-D of FIG. 24 illustrates a cross-section view of catheter assembly 120. Section E-E of FIG. 24 illustrates a cross-sectional of catheter assembly 120 as one example of geometric constraints that may influence the geometry for tubular isolating material 170.

Isolating medium 170 may be geometrically tubular as depicted by section callout C-C of FIG. 23. The outer diameter 180 of tubular isolating medium 170 may be approximately equal to the inner diameter 140-ID of inner tube component 140. Tubular isolating material 170 may be comprised of a material capable of stretching to an inner diameter 182 of at least the outer diameter 140-OD of inner tube component 140. It should be noted that the thickness of tubular isolating material 170 ([outer diameter 180/2]–[inner diameter 182/2]) may be influenced by the channel size 174 between inner tube component 140 and outer tube component 160 such that tubular isolating material 170 can travel from the proximal to the distal end of catheter assembly 120 as was previously described in embodiments disclosed within this document, such as for example, FIG. 14. It should be noted that some lubrication may be used within channel 174 to aid in the travel of isolating film material 170.

Isolating medium or material 170 may be made of polymers including but not limited to: polyethylene, polypropylene, polytetraflu (PTFE), polyvinylchloride (PVC), silicones and polymers therein, polyethylene terephthalate (PET), polyether sulfone (PES), polyamide-nylon, and polyurethanes. The aforementioned materials do not limit the possible material characteristics or possible materials of isolating medium or material 170 in any of the aforementioned embodiments of the catheter assembly. Isolating medium or material 170 may have non-limiting material characteristics including, but not limited to: possible processing to a micron diameter to produce a thin film, may be non-biodegradable, does not promote mineralization or encrustation, may be bio-inert, may be hydrophobic and/or hydrophilic, may have minimal leaching of material components, may have long storage and shelf-life, and may be sterilizable.

Outer tube component 160 and inner tube component 140 may be composed of the following materials including, but not limited to polyether ether ketone (PEEK), lactic acid, glycolic acid, polymethylmethacrylate (PMMA), bis-GMA based polymers. The aforementioned inner tube component 140 and outer tube component 160 materials do not limit the possible material characteristics or material of the inner tube component 140 and outer tube component 160 in the present invention and all the aforementioned embodiments of the catheter assembly 120.

Aspects of the present invention provide an indwelling percutaneous nephrostomy catheter with a supply of disposable isolating medium or material film. The device's distinguishing function is that a replaceable supply of isolating medium or material film covers the fluid-exposed portions of the catheter and can be replaced at regular intervals to prevent encrustation and biofilm formation, which precludes catheter obstruction that may lead to clinical infection. The disposal of these films can occur without removing the catheter itself. The device aims to decrease the rate of repeat intervention, decrease infection rates, decrease costs associated with PCN complications, and, most importantly, improve quality of care for patients.

The mechanism of disposable isolating medium or material film in nephrostomy catheters, according to aspects of the invention, has broad significance as the same design can be applied to other indwelling percutaneous catheters. In fact, the catheter utilized in percutaneous nephrostomy may also be used in percutaneous cholecystostomy, percutaneous suprapubic cystostomy, and percutaneous abscess drainage. Aspects of the present invention contrast to existing drainage catheters and techniques that may require routine or emergent exchanges due to catheter obstruction, much as they do in percutaneous nephrostomy.

Aspects of the invention address the unmet need for drainage catheters that do not require catheter exchanges, or replacements. The importance of this need is emphasized in the clinical setting where patients requiring routine or emergent exchanges are subject to repeat fluoroscopy (or radiation exposure), repeat anesthesia with its associated risks, and re-intervention, which comes with its own set of complications. With re-intervention, there may be complications including but not limited to septic shock, vascular injury, and gastrointestinal bowel transgression. Aspect of the invention can obviate the need for routine catheter exchanges and thus can completely avert repeat radiation, repeat anesthesia, and re-intervention. Additionally, aspects of the invention have immediate applications in percutaneous cholecystostomy, suprapubic cystostomy, cyst drainage, pseudocyst drainage, pleural space drainage, abdominal cavity drainage, thoracic cavity drainage, or drainage of any other fluid-containing cavity also including abscesses.

Additional embodiments are illustrated in FIGS. 25-33. Drainage catheter assemblies are useful in providing flow diversion when natural body conduits are obstructed and lead to pathologic build-up of fluid and pressure. Drainage catheter assemblies provide an outlet when the natural outlet lumen is compromised due to pathology, obstructed, or otherwise unable to be regulated. For example, drainage catheters assemblies can be used to provide a percutaneous outlet for urine collected in a hydronephrotic kidney, resulting from a distal ureteral obstruction by a kidney stone.

Existing catheter assemblies used for drainage are single tube and single lumen with a distal end lumen with a limited number of discrete side-holes extending through the tubular shaft wall. These catheter assemblies are retained within the specified space via Cope loop assembly, Malecot tip assembly, or other similar anti-dislodgement catheter tip assemblies.

As with any catheter assembly, the need to maintain the structural integrity, sterility, and patency are critically important to the catheter assembly's functional application. The present inventor recognizes, among other things, that current standard-of-care drainage catheter assemblies may be prone to blockage at, for example, and around the distal portions of the catheter exposed to the body environment as well as along any point the drained material courses from the draining lumen(s) throughout the catheter assembly. Blockage complications may be a result of biofilm accumulation, mineral encrustation, biological stones, and accumulation of other debris, among other things. Prolonged blockage without resolution may lead to infection, organ damage, sepsis, and other associated complications.

To resolve complications related to blockage, existing catheter assemblies might be manipulated, repositioned, or exchanged and replaced. They may also be de-clogged mechanically, or by use of chemicals. Repeat procedures require patients to undergo anesthesia, which subjects them to associated risks.

Though existing drainage catheter assemblies can provide effective means to, for example, drain internal cavities or organs, there exists a need in the art to improve drainage catheters and the techniques used to provide the desired drainage. Aspects of the present invention provide improvements to the existing art of drainage catheters and their methods of use.

In order to minimize complications related to catheter assembly blockage from occurring, the present invention comprises catheter assemblies, include a disposable layer of film that isolates the otherwise fluid-exposed portions of the catheter from the fluid it drains. This disposable film can be removed at regular intervals and obviates the need for catheter exchanges as the isolating disposable film, rather than the catheter itself, is removed. The principal characteristic of the disposable film is that it is relatively impermeable to fluid, for example, bodily fluids.

The following catheter assembly can be inserted into body conduits, body cavities, or other target organs, to relieve obstruction, allow for fluid diversion, provide access for other procedures, or administer fluids for therapeutic or diagnostic purposes, among other potential uses. This minimally invasive catheter assembly obviates the need for open and invasive surgical procedures. With any drainage catheter, there are anti-dislodgement mechanisms that are integrated into the catheter design to prevent the catheter from unintentionally being removed from the targeted space. There are many variations on anti-dislodgement mechanisms that include, but are not limited to: Malecot tips, pig-tail tips, inflatable balloon tips.

The principal embodiment of the invention is a drainage catheter assembly comprising of an: inner tube; an outer tube, an interspace between the inner and outer tube; a hub at the proximal end of the drainage catheter that can connect the inner and outer tube; and, a hub that can contain a film contained within a geometrically accommodating reservoir. Herein, the outer tube and the inner tube in their various anti-dislodgement embodiments may be assembled with or integrated into the aforementioned embodiments.

Figure 25:
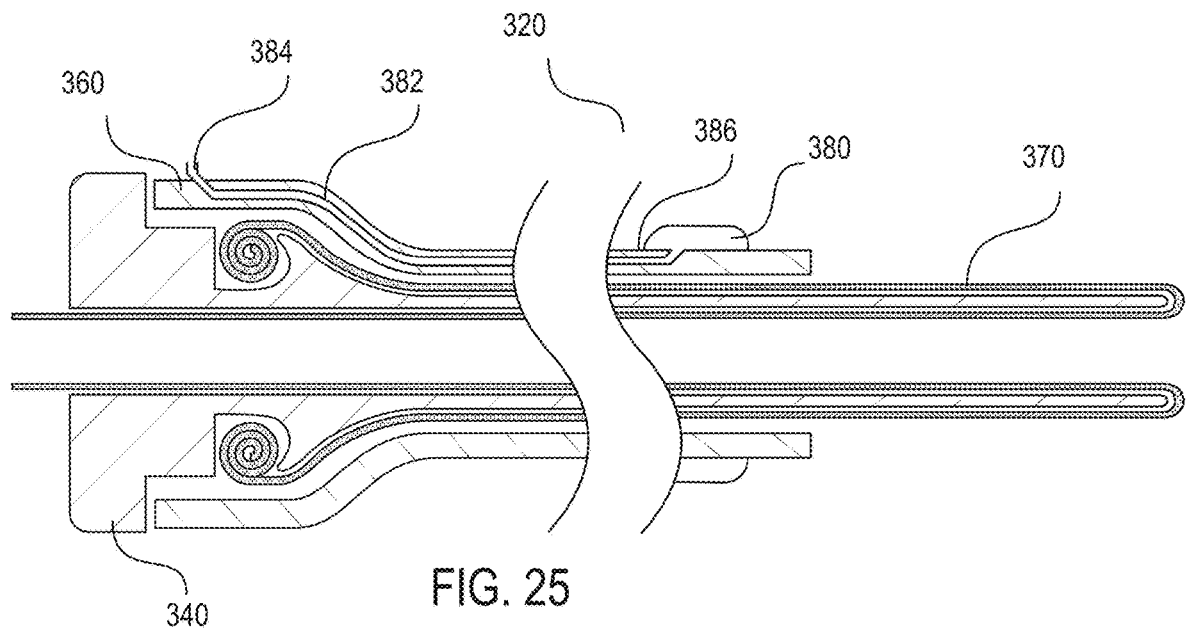
FIG. 25 illustrates a side view of the outer tube component of the catheter assembly with an inflatable balloon at the distal tip of the outer tube, in accordance with at least one embodiment of the invention.

FIG. 25 illustrates another embodiment of a catheter assembly 320. For the embodiments regarding the catheter assembly 320, the features are referred to using similar reference numerals under the "3xx" series of reference numerals, rather than "1xx" and "2xx" as used in the previous embodiments. Accordingly, certain features of the catheter assembly 320 that were already described above with respect to the catheter assembly 120 and the catheter assembly 220 may be described in lesser detail, or may not be described at all. FIG. 25 specifically illustrates a side view of the outer tube component 360 of the catheter assembly with an inflatable balloon 380 at the distal tip of the outer tube component 360. This inflatable balloon 380 prevents dislodgement of the catheter assembly 320 from the cavity it is initially placed in. This mechanism consists of a channel 384 within the outer tube component 360 that extends from the proximal portion of the outer tube component 360, to its distal tip. A two-way valve may be present at along any point in this channel 384 to prevent undesired backflow. The channel 384 may be open to the outside environment. The exposed portion of the channel 384 may have a luer lock, onto which a syringe can be fastened to. The inflation of the balloon 380 can be with a liquid or gas. The syringe may contain a gas or a fluid that can be injected into the channel 384, and into the distal balloon 380. On injecting either a gas or fluid, the uninflated balloon 380 will inflate as show in the figure. The syringe may also be used to remove either gas or fluid to deflate the balloon 380, so that the catheter assembly 320 can be removed from the body without additional resistance. A radio-opaque marker 386 may be located immediately proximal to the balloon 380 to confirm that the balloon 380 is in the proper anatomical position prior to inflation or deflation of the balloon 380.

Figure 26:
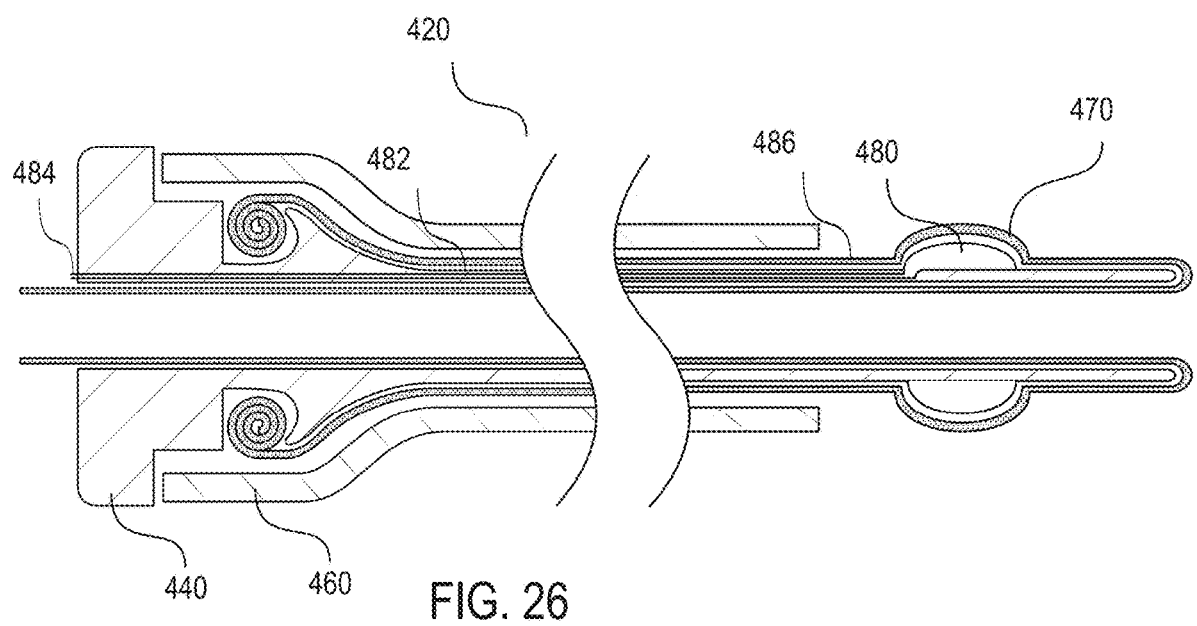
FIG. 26 illustrates a side view of the inner tube component of the catheter assembly with an inflatable balloon at the distal tip of the inner tube, in accordance with at least one embodiment of the invention.

FIG. 26 illustrates another embodiment of a catheter assembly 420. For the embodiments regarding the catheter assembly 420, the features are referred to using similar reference numerals under the "4xx" series of reference numerals, rather than "1xx", "2xx", and "3xx" as used in the previous embodiments. Accordingly, certain features of the catheter assembly 420 that were already described above with respect to the catheter assembly 120, the catheter assembly 220, and the catheter assembly 320 may be described in lesser detail, or may not be described at all. FIG. 26 specifically illustrates a side view of the inner tube component 440 of the catheter assembly 420 with an inflatable balloon 480 at the distal tip of the inner tube component 440. The inflatable balloon 480 prevents dislodgement of the catheter assembly 420 from the cavity it is initially placed in. The inflation of the balloon 480 can be with liquid or gas. The mechanism for balloon 480 inflation involves connecting a syringe to the channel 484 located proximally on the inner tube component 440. A valve may be present at any point along the channel 484 to prevent undesired backflow. The channel 484 may have a lock onto which a syringe can be fastened to. By injecting gas or fluid, the uninflated balloon 480 will begin to fill and inflate as shown in the figure. A syringe may be used to remove either the gas or fluid to deflate the balloon 480 at the time the catheter assembly 420 requires removal from the target space without resistance. A radio-opaque marker 486 may be located immediately proximal to the balloon 480 to confirm that the balloon 480 is in the proper anatomical position prior to inflation or deflation of the balloon 480.

Figure 27:
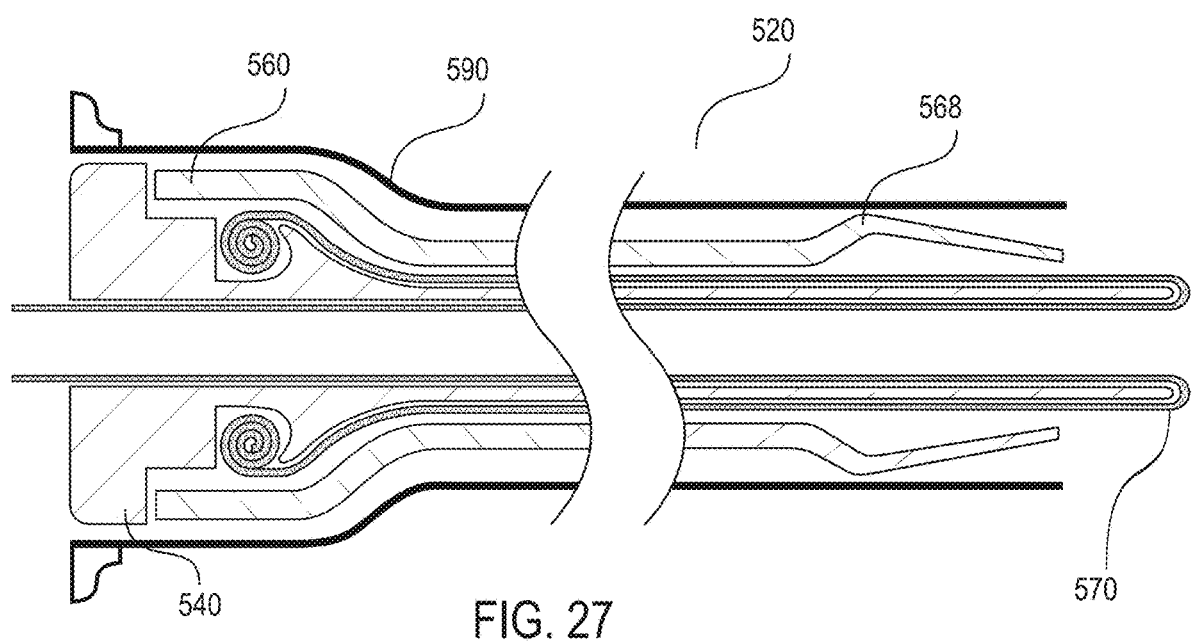
FIG. 27 illustrates a side view of the outer tube component of the catheter assembly with its distal tip divided into at least two or more separate arms compressed and confined by an outer sheath, in accordance with at least one embodiment of the invention.
Figure 28:
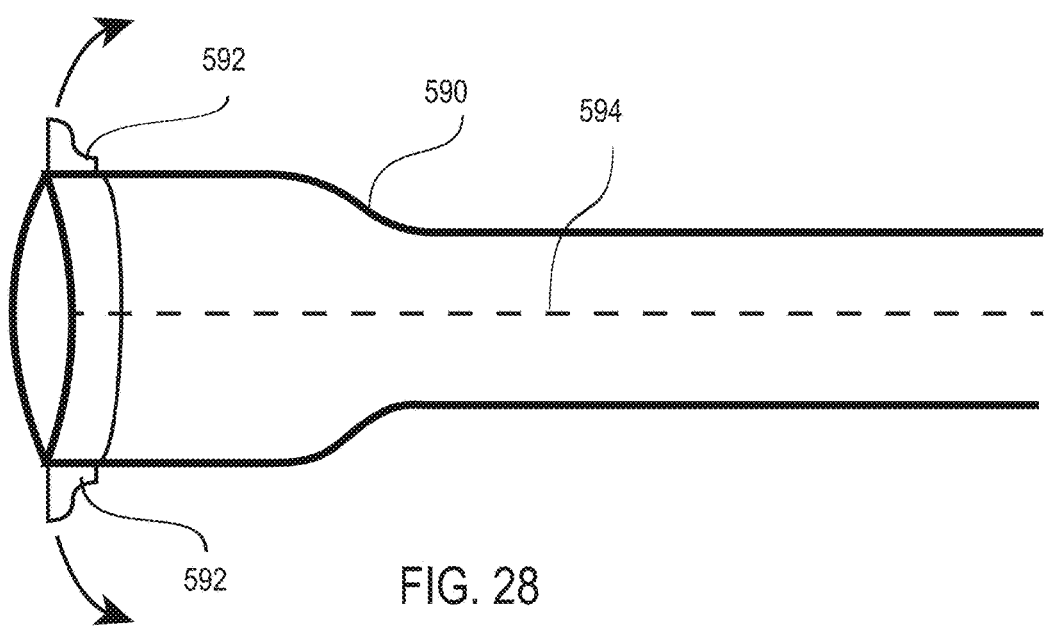
FIG. 28 illustrates a side view of the sheath component of the catheter assembly, in accordance with at least one embodiment of the invention.
Figure 29:
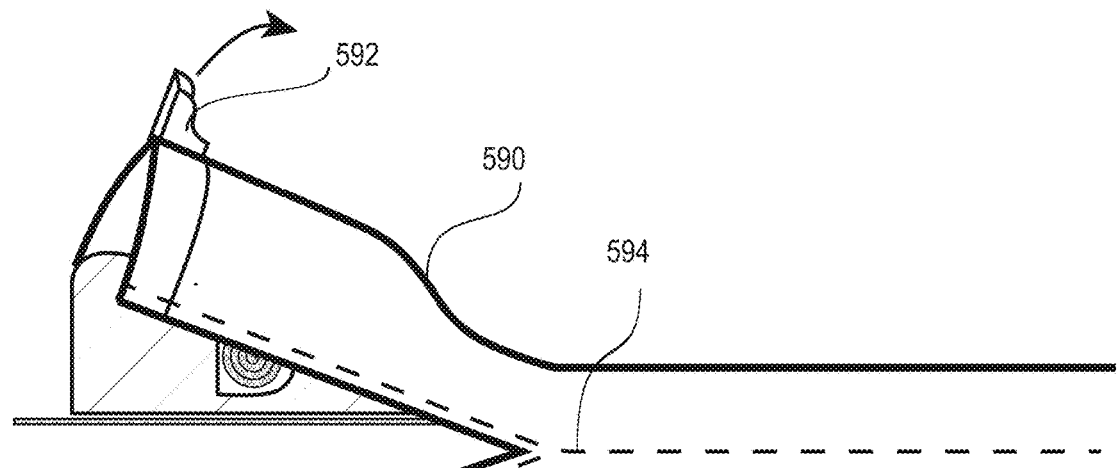
FIG. 29 illustrates a side view of the sheath component of the catheter assembly, in accordance with at least one embodiment of the invention.
Figure 30:
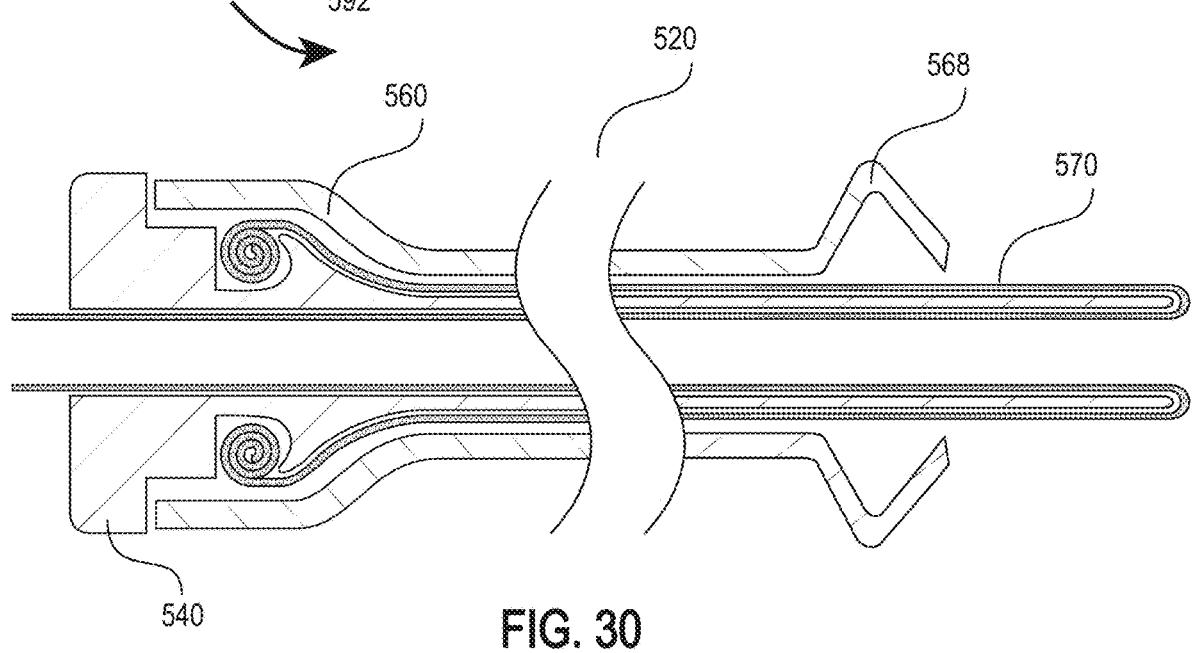
FIG. 30 illustrates a side view of the outer tube component of the catheter assembly with its distal tip divided into at least two or more separated arms in the resting position and unconfined to the dimensions of the outer sheath of the catheter assembly, in accordance with at least one embodiment of the invention.

FIGS. 27-30 illustrate another embodiment of a catheter assembly 520. For the embodiments regarding the catheter assembly 520, the features are referred to using similar reference numerals under the "5xx" series of reference numerals, rather than "1xx", "2xx", "3xx", and "4xx" as used in the previous embodiments. Accordingly, certain features of the catheter assembly 520 that were already described above with respect to the catheter assembly 120, the catheter assembly 220, the catheter assembly 320, and the catheter assembly 420 may be described in lesser detail, or may not be described at all. FIG. 27 specifically illustrates a side view of the outer tube component 560 of the catheter assembly 520 with its distal tip divided into at least two or more separate arms 568 compressed and confined by an outer sheath 590. The at least two or more separate arms 568 may be pre-shaped to fold proximally onto itself as shown in FIG. 30. The outer sheath 590 acts to compress the outer tube component 560 distal tip arms 568, such that it can be inserted into the target anatomical space without deformation. The sheath 590 may be a peel-away sheath, such that it can be removed and pulled away from the catheter without removing the catheter assembly 590 from its final placement within the target anatomical space. In removing the outer sheath 590, as with a peel-away sheath, the at least two or more separate and unconfined arms 568 of the distal tip assume its resting position which is to fold on itself as shown in FIG. 30, which acts as an anti-dislodgement mechanism.

FIG. 28 illustrates a side view of the sheath 590 component of the catheter assembly 120, which is composed of two winged tips 592 at the proximal portion of the sheath 590 that an operator can pull in opposing directions perpendicular to the angle of insertion of the catheter assembly 120. Applying force as such will cause the sheath to split along its serrated connection 594, which run along opposing sides of the sheath 590 from the proximal point of the sheath 590 to a distal tip on the sheath 590.

FIG. 29 illustrates a side view of the sheath 590 component of the catheter assembly 120 as the sheath 590 is being pulled apart by use of the two winged tips 592 along the perforated edges 594.

FIG. 30 illustrates a side view of the outer tube component 560 component of the catheter assembly 520 with its distal tip divided into at least two or more separated arms 568 in the resting position and unconfined to the dimensions of the outer sheath of the catheter assembly 520. This view illustrates the catheter assembly 520 subsequent to the removal of the outer sheath 590 of FIG. 27, FIG. 28, and FIG. 29. While there at least two extensions 568 illustrated, there are at least one or more in iterations of this outer tube component 560.

Figure 31:
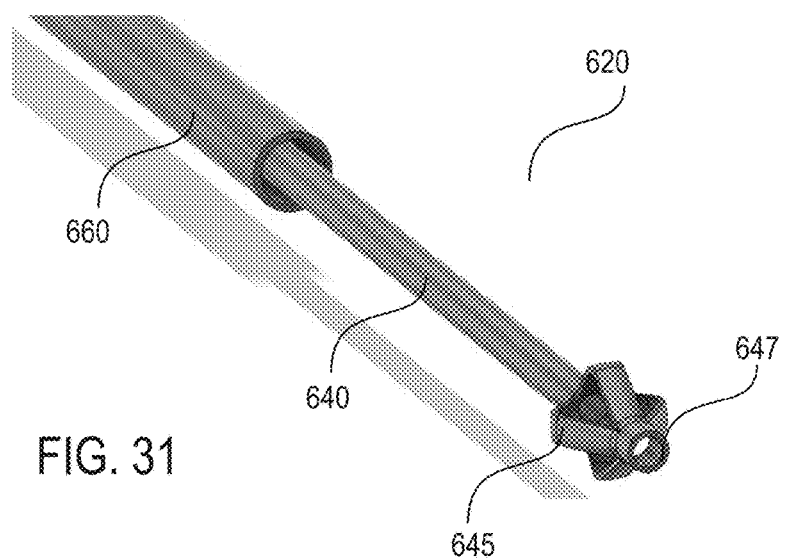
FIG. 31 specifically illustrates a perspective view of a catheter assembly, in accordance with at least one embodiment of the invention.
Figure 32:
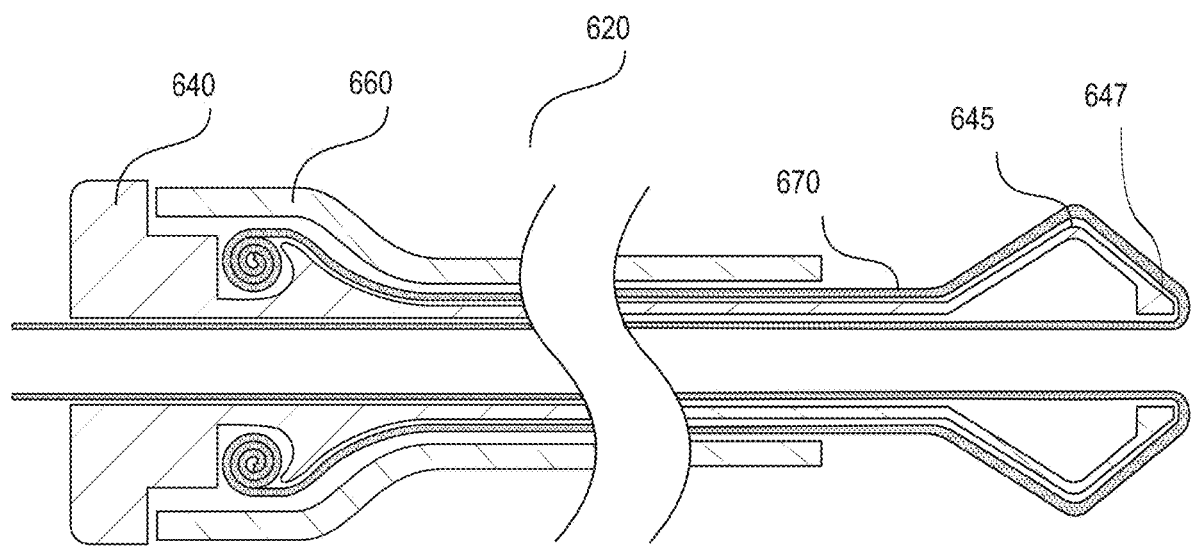
FIG. 32 illustrates a side view of the inner tube component of the catheter assembly from FIG. 31 with its distal tip divided into at least two or more arms, in accordance with at least one embodiment of the invention.

FIGS. 31 and 32 illustrate another embodiment of a catheter assembly 620. For the embodiments regarding the catheter assembly 620, the features are referred to using similar reference numerals under the "6xx" series of reference numerals, rather than "1xx", "2xx", "3xx", "4xx", and "5xx" as used in the previous embodiments. Accordingly, certain features of the catheter assembly 620 that were already described above with respect to the catheter assembly 120, the catheter assembly 220, the catheter assembly 320, the catheter assembly 420, and the catheter assembly 520 may be described in lesser detail, or may not be described at all. FIG. 31 specifically illustrates a perspective view of a catheter assembly 620. FIG. 32 specifically illustrates a side view of the inner tube component 640 of the catheter assembly 620 with its distal tip divided into multiple arms 645 in the resting position and unconfined to the dimensions of the outer sheath of the catheter assembly 620. These distal tip arms 645 or extensions are covered by the isolating material or medium 670 that covers the distal tip arms 645. These arms 645 coalesce at the distal tip 647, which has a tapered ending. This tapered ending 647 allows for a rigid stiffener to be inserted into the draining lumen of the inner tube component 640. The tapered ending 647 also allows for the system to be fully straightened prior to insertion into the target anatomical site. Alternatively, the catheter assembly 620 may be encased by a sheath as illustrated and described in FIG. 28 and unsheathed by the same mechanism as illustrated and described in FIG. 29.

Figure 33:
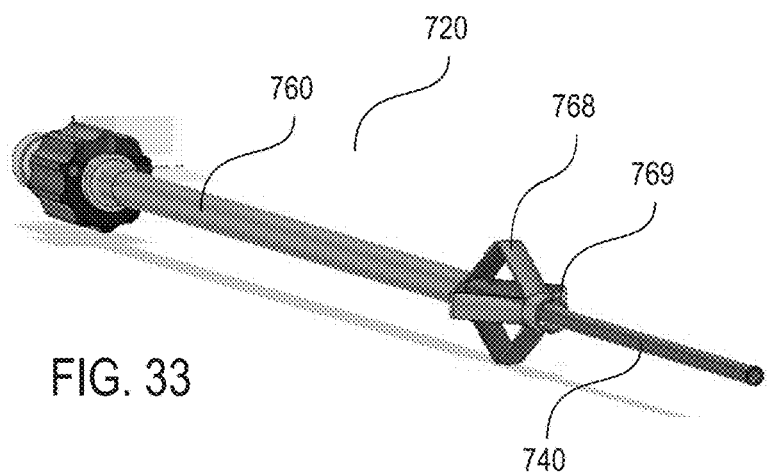
FIG. 33 illustrates a perspective view of a catheter assembly, in accordance with at least one embodiment of the invention.
Figure 34:
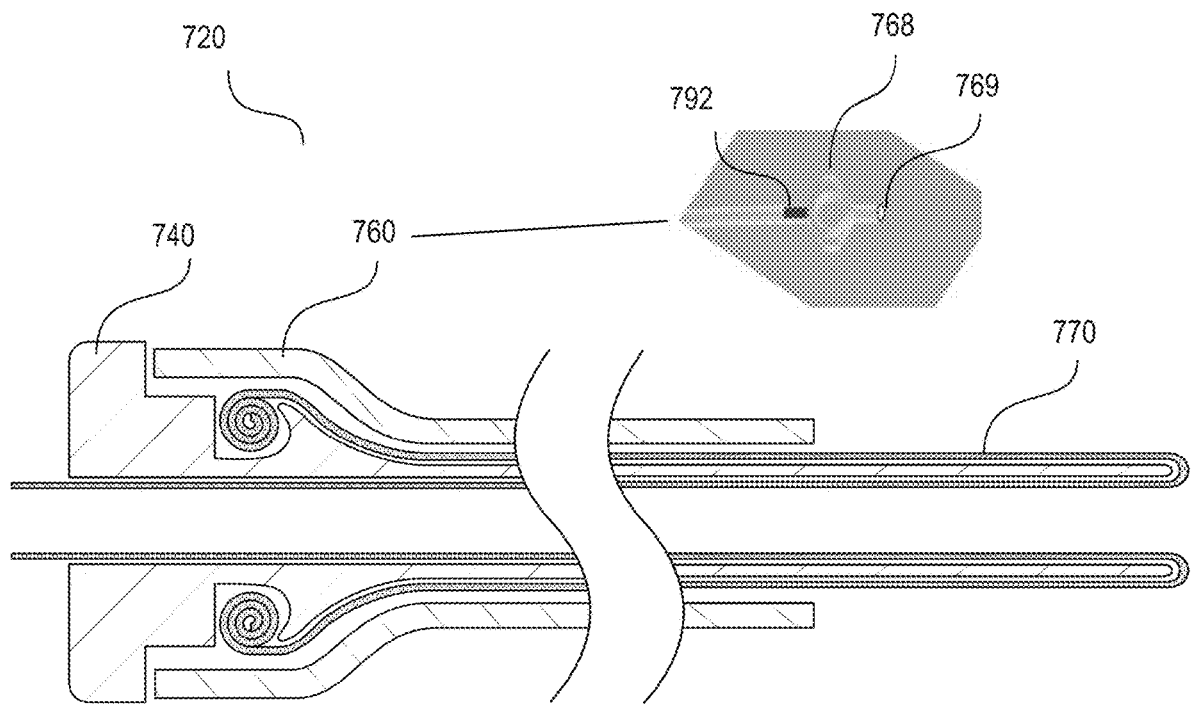
FIG. 34 illustrates a side view of the outer tube component of the catheter assembly from FIG. 33 with the distal tip divided into at least two or more arms, in accordance with at least one embodiment of the invention.

FIGS. 33 and 34 illustrate another embodiment of a catheter assembly 720. For the embodiments regarding the catheter assembly 720, the features are referred to using similar reference numerals under the "6xx" series of reference numerals, rather than "1xx", "2xx", "3xx", "4xx", "5xx", and "6xx" as used in the previous embodiments. Accordingly, certain features of the catheter assembly 720 that were already described above with respect to the catheter assembly 120, the catheter assembly 220, the catheter assembly 320, the catheter assembly 420, the catheter assembly 520, and the catheter assembly 620 may be described in lesser detail, or may not be described at all. FIG. 33 specifically illustrates a perspective view of the outer tube component 760 of the catheter assembly 720. The outer tube component 760 may include a distal tip divided into at least two or more arms 768 confined to the dimensions of the outer sheath (not shown) of the catheter assembly 760. FIG. 34 illustrates a side view of the outer tube component 760 of the catheter assembly 720 with the distal tip divided into at least two or more arms 768 unconfined to the dimensions of the outer sheath (not shown) of the catheter assembly 720 and assuming its preformed shape 768 akin to a Malecot tip, but with an open-end hole 769. The open-end hole 769 may be open to draining fluid as opposed to a traditional Malacot tip with a blind ending at its distal tip. A radio-opaque marker 792 may be present proximal to the distal arms 768.

Aspects of this invention provide various unique features for a catheter assembly. The catheter assembly may include a disposable film or isolating medium travelling from the outer diameter, inverting into the inner diameter (or inner lumen) of the catheter and travelling outside of the proximal hub of the catheter (and outside the patient). This provides a mechanical anti-occlusion mechanism that insulates or isolates the catheter from the environment the catheter is placed in. The isolating medium may be removed and simultaneously replaced by isolating medium in the film reservoir. The reservoir may contain a disposable film or isolating medium. Additionally, the catheter assembly may include a locking mechanism between the inner tube component and the outer tube component and connected at the proximal hub. Generally, catheters are not double-tubed or tube-in-a-tube and if they are, catheters are not joined at the proximal end as described and detailed. Whether the locking mechanism is a lock and key mechanism or screwed into be secured, the outer tube component and the inner tube component must be connected at the proximal hub.

Aspects of this invention provide additional various unique features for a catheter assembly. The two-tube system (inner tube component and outer tube component) may include an anti-dislodgement mechanism, such as a balloon or Malecot tip. The anti-dislodgement mechanism may be located on the inner tube component or the outer tube component of the catheter assembly. The anti-dislodgement mechanism may include at least two or more arms that fold onto itself when it is in a resting position and initially constrained to the shape of the catheter by a sheath. The anti-dislodgement mechanism may also include an inflatable balloon located on either the inner tube component or the outer tube component of the catheter assembly.

The catheter assembly as described herein creates opportunities for improved patient care, improved clinical outcomes, and cost-savings for hospitals. Whereas patients currently require emergency room admissions, emergent catheter exchange reoperation, and inpatient hospitalization to treat infection, the catheter assembly as described herein aims to significantly decrease the incidence of complications through its anti-occlusion mechanism, which is inherently anti-biofilm and anti-encrustation. Where the current standard of care is re-operation for catheter-exchange, the catheter assembly as described herein offers a non-invasive, bedside alternative. There are no devices on the market with an anti-occlusive, anti-biofilm, and anti-encrustation mechanism as the catheter assembly as described herein.

Instead, modern research in catheter development has focused on static designs: antimicrobial materials, antimicrobial coatings, and anti-fouling chemical applications to name a few, which have demonstrated incremental improvement in catheter life but without long-term sustainability. The catheter assembly as described herein presents a unique solution with its mechanical anti-occlusion mechanism, which makes the catheter assembly as described herein effectually impervious to catheter occlusion.

While the aspects described herein have been discussed with respect to specific examples including various modes of carrying out aspects of the disclosure, those skilled in the art will appreciate that there are numerous variations and permutations of the above described systems and techniques that fall within the spirit and scope of the invention. For example, one of ordinary skill in the art will appreciate that the steps illustrated in the illustrative figures may be performed in other than the recited order, and that one or more steps illustrated may be optional in accordance with aspects of the disclosure. Further, one of ordinary skill in the art will appreciate that various aspects described with respect to a particular figure may be combined with one or more other aspects, in various combinations, without departing from the invention.

While the preferred embodiments of the invention have been shown and described, it will be apparent to those skilled in the art that changes and modifications may be made therein without departing from the spirit of the invention, the scope of which is defined by this description.

I claim:

1. A catheter assembly comprising:
an elongated outer tube component having a proximal end and a distal end;
an elongated inner tube component having a proximal end and a distal end, and positioned within the elongated outer tube component; and
an isolating medium positioned over the elongated inner tube component isolating at least the distal end of the elongated inner tube component from bodily fluids,
wherein the isolating medium comprises a first isolating medium, wherein the assembly further comprises a second isolating medium that is configured to replace the first isolating medium as the first isolating medium is being removed.

2. The catheter assembly of claim 1, wherein the isolating medium comprises a removable isolating medium.

3. The catheter assembly of claim 1, further comprising a locking mechanism located between the elongated inner tube component and the elongated outer tube component.

4. The catheter assembly of claim 3, wherein the locking mechanism is a lock and key mechanism between the elongated inner tube component and the elongated outer tube component.

5. The catheter assembly of claim 3, wherein the locking mechanism is a screw connector between the elongated inner tube component and the elongated outer tube component.

6. The catheter assembly of claim 1, wherein at least one of the elongated outer tube component and the elongated inner tube component comprises a cavity for the isolating medium.

7. The catheter assembly of claim 1, wherein the catheter assembly is utilized for a kidney.

8. The catheter assembly of claim 1, wherein the catheter assembly comprises a fluid treatment.

9. The catheter assembly of claim 8, wherein the fluid treatment comprises one of a liquid treatment and a gas treatment.

10. The catheter assembly of claim 1, wherein the isolating medium comprises a plastic material.

11. The catheter assembly of claim 1 further comprising an anti-dislodgement mechanism that includes at least two arms located in one of the elongated inner tube component and the elongated outer tube component.

12. The catheter assembly of claim 1 further comprising an anti-dislodgement mechanism that includes an inflatable balloon located in one of the elongated inner tube component and the elongated outer tube component.

13. A method of introducing or removing a fluid from a body cavity, the method comprising:
inserting a catheter assembly into a body cavity, the catheter assembly comprising: an outer tube component having a proximal end and a distal end;
an inner tube component having a proximal end and a distal end, and positioned within the outer tube component; and
an isolating medium positioned over the inner tube component isolating at least the distal end of the inner tube component from bodily fluids;
withdrawing a bodily fluid from the body cavity; and
removing the isolating medium from at least the distal end of the inner tube component,
wherein the isolating medium comprises a first isolating medium wherein the assembly further comprises a second isolating medium that is configured to replace the first isolating medium as the first isolating medium is being removed.

14. The method of claim 13, wherein the first isolating medium is connected to the second isolating medium, wherein replacing the first isolating medium with the second isolating medium comprises extracting the first isolating medium from the catheter assembly and therein drawing the second isolating medium over at least the distal end of the inner tube component.

15. The method of claim 13, wherein the catheter assembly further comprises a locking mechanism located between the inner tube component and the outer tube component.

* * * * *